United States Patent
Yoneki et al.

(10) Patent No.: US 10,945,997 B2
(45) Date of Patent: Mar. 16, 2021

(54) POLYMER DERIVATIVE OF MACROLIDE IMMUNOSUPPRESSANT

(71) Applicant: Nippon Kayaku Kabushiki Kaisha, Tokyo (JP)

(72) Inventors: Nao Yoneki, Tokyo (JP); Akihiro Sekiguchi, Tokyo (JP); Kana Mizunuma, Tokyo (JP); Yuki Kobayashi, Tokyo (JP); Junpei Konno, Tokyo (JP); Kan Saiga, Tokyo (JP); Keiichirou Yamamoto, Tokyo (JP)

(73) Assignee: Nippon Kayaku Kabushiki Kaisha, Tokyo (JP)

( * ) Notice: Subject to any disclaimer, the term of this patent is extended or adjusted under 35 U.S.C. 154(b) by 220 days.

(21) Appl. No.: 16/066,692

(22) PCT Filed: Dec. 19, 2016

(86) PCT No.: PCT/JP2016/087774
§ 371 (c)(1),
(2) Date: Jun. 28, 2018

(87) PCT Pub. No.: WO2017/119272
PCT Pub. Date: Jul. 13, 2017

(65) Prior Publication Data
US 2020/0155518 A1 May 21, 2020

(30) Foreign Application Priority Data
Jan. 8, 2016 (JP) .............................. JP2016-002678

(51) Int. Cl.
| | |
|---|---|
| *A61K 31/436* | (2006.01) |
| *A61K 47/64* | (2017.01) |
| *A61K 47/60* | (2017.01) |
| *C08G 69/48* | (2006.01) |

(52) U.S. Cl.
CPC ............ *A61K 31/436* (2013.01); *A61K 47/60* (2017.08); *A61K 47/645* (2017.08); *C08G 69/48* (2013.01)

(58) Field of Classification Search
CPC ...... C08G 69/40; A61K 47/60; A61K 47/645; A61K 31/706; A61P 29/00
See application file for complete search history.

(56) References Cited

U.S. PATENT DOCUMENTS

| | | | |
|---|---|---|---|
| 5,247,076 A | 9/1993 | Goulet et al. | |
| 5,344,925 A | 9/1994 | Goulet et al. | |
| 5,922,729 A | 7/1999 | Chang et al. | |
| 6,395,254 B1 | 5/2002 | Sinn et al. | |
| 10,357,573 B2 | 7/2019 | Onda et al. | |
| 2004/0151690 A1 | 8/2004 | Nakanishi et al. | |
| 2006/0099265 A1 | 5/2006 | Shimizu et al. | |
| 2006/0134166 A1* | 6/2006 | Luthra | A61L 29/048 424/422 |
| 2009/0012252 A1 | 1/2009 | Masuda et al. | |
| 2009/0156742 A1 | 6/2009 | Shimizu et al. | |
| 2009/0239782 A1 | 9/2009 | Nakamura et al. | |
| 2010/0234537 A1 | 9/2010 | Kitagawa et al. | |
| 2012/0116051 A1 | 5/2012 | Kitagawa et al. | |
| 2013/0281638 A1 | 10/2013 | Ueno et al. | |
| 2014/0142167 A1 | 5/2014 | Shimizu et al. | |
| 2015/0011715 A1 | 1/2015 | Nakamura et al. | |
| 2016/0279164 A1 | 9/2016 | Nakamura et al. | |
| 2018/0050112 A1 | 2/2018 | Onda et al. | |
| 2018/0334540 A1 | 11/2018 | Sekiguchi et al. | |

FOREIGN PATENT DOCUMENTS

| | | |
|---|---|---|
| EP | 2070971 A1 | 6/2009 |
| EP | 3263107 A1 | 1/2018 |
| JP | 2000-502109 A | 2/2000 |
| WO | 93/005059 A1 | 3/1993 |
| WO | 99/03860 A1 | 1/1999 |
| WO | 03/000771 A1 | 1/2003 |
| WO | 2004/082718 A1 | 9/2004 |
| WO | 2005/079861 A2 | 9/2005 |
| WO | 2006/120914 A1 | 11/2006 |
| WO | 2007/111211 A1 | 10/2007 |
| WO | 2008/041610 A1 | 4/2008 |
| WO | 2010/131675 A1 | 11/2010 |
| WO | 2013/157664 A1 | 10/2013 |
| WO | 2016/021407 A1 | 2/2016 |

(Continued)

OTHER PUBLICATIONS

European communication dated Aug. 13, 2019 in corresponding European patent application No. 16883771.4.
European communication dated Jul. 1, 2019 in co-pending European patent application No. 16866237.7.
Torchilin, "Block Copolymer Micelles as a Solution for Drug Delivery Problems", Expert Opinion on Therapeutic Patents, vol. 15, No. 1, pp. 63-75, 2005.
Office action dated Apr. 17, 2020 in co-pending U.S. Appl. No. 15/776,802.
International Search Report and Written Opinion dated Feb. 7, 2017 in corresponding PCT application No. PCT/JP2016/087774.
Allen et al., "Cellular internalization of PCL20-b-PEO44 block copolymer micelles", Biochimica et Biophysica Acta, vol. 1421, pp. 32-38, 1999.

(Continued)

*Primary Examiner* — Robert S Jones, Jr.
(74) *Attorney, Agent, or Firm* — Nields, Lemack & Frame, LLC

(57) ABSTRACT

An object of the invention is to obtain a preparation which shows enhanced effectiveness and safety compared to tacrolimus, has the concentration in blood maintained at a constant level without individual differences, whereby the control of the amount of administration depending on the blood kinetics (blood trough concentration) becomes unnecessary. The present invention relates to a polymeric derivative of tacrolimus, in which a polyethylene glycol segment and an alcoholic hydroxy group of tacrolimus are bonded to side-chain carboxy groups of a polyaspartic acid derivative.

25 Claims, 5 Drawing Sheets

(56) References Cited

FOREIGN PATENT DOCUMENTS

WO    2016/136641 A1    9/2016

OTHER PUBLICATIONS

Allen et al., "PCL-b-PEO Micelles as a Delivery Vehicle for FK506: Assessment of a Functional Recovery of Crushed Peripheral Nerve", Drug Delivery, vol. 7, pp. 139-145, 2000.
Choi et al., "Effects of Water-soluble Tacrolimus-PEG Conjugate on Insulin-dependent Diabetes Mellitus and Systemic Lupus Erythematosus", Archives of Pharmacal Research, vol. 34, No. 8, pp. 1301-1310, 2011.
Chung et al., "Preparation of Highly Water Soluble Tacrolimus Derivatives: Poly(Ethylene Glycol) Esters as Potential Prodrugs", Archives of Pharmacal Research, vol. 27, No. 8, pp. 878-883, 2004.
Hashimoto et al., "Effects of Intestinal and Hepatic Metabolism on the Bioavailability of Tacrolimus in Rats", Pharmaceutical Research, vol. 15, No. 10, pp. 1609-1613, 1998.
Kaplan et al., "Low Bioavailability of Cyclosporine Microemulsion and Tacrolimus in a Small Bowel Transplant Recipient", Transplantation, vol. 67, No. 2, pp. 333-338, 1999.
Meissner et al., "Nanoparticles in Inflammatory Bowel Disease: Particle Targeting Versus pH-Sensitive Delivery", International Journal of Pharmaceutics, vol. 316, pp. 138-143, 2006.
Wang et al., "Micelles of Methoxy Poly(ethylene glycol)-Poly(e-caprolactone) as a Novel Drug Delivery Vehicle for Tacrolimus", Journal of Biomedical Nanotechnology, vol. 9, pp. 147-157, 2013.
Materials on PROGRAPH capsules (0.5 mg, 1 mg, 5 mg) and PROGRAPH injectable solution (5 mg) of Fujisawa Pharmaceutical Co., Ltd. (currently Astellas Pharma Inc.), p. 53, Summary of application materials for department meeting deliberation and approval of Jun. 2001.
nternational Search Report and Written Opinion dated Dec. 13, 2016 in co-pending PCT application No. PCT/JP2016/083417.
Taiwanese communication, with English translation, dated Mar. 3, 2020 in co-pending Taiwanese patent application No. 105137594.
Adams et al., "Amphiphilic Block Copolymers for Drug Delivery", Journal of Pharmaceutical Sciences, vol. 92, No. 7, pp. 1343-1355, Jul. 2003.
European communication dated May 27, 2020 in co-pending European patent application No. 16866237.7.
Japanese communication, with English translation, dated Aug. 18, 2020 in corresponding Japanese patent application No. 2017-560083.
Japanese communication, with English translation, dated Jul. 7, 2020 in co-pending Japanese patent application No. 2017-551846.
Taiwanese communication, with English translation, dated Jun. 20, 2020 in corresponding Taiwanese patent application No. 106100175.
Final rejection dated Sep. 21, 2020 in co-pending U.S. Appl. No. 15/776,802.
Taiwanese communication, with English translation, dated Jul. 2, 2020 in co-pending Taiwanese patent application No. 105137594.
Nehoff et al., "Nanomedicine for Drug Targeting: Strategies Beyond the Enhanced Permeability and Retention Effect", International Journal of Nanomedicine, vol. 9, pp. 2539-2555, 2014.
European communication dated Oct. 28, 2020 in corresponding European patent application No. 16883771.4.

* cited by examiner

[Figure 1]
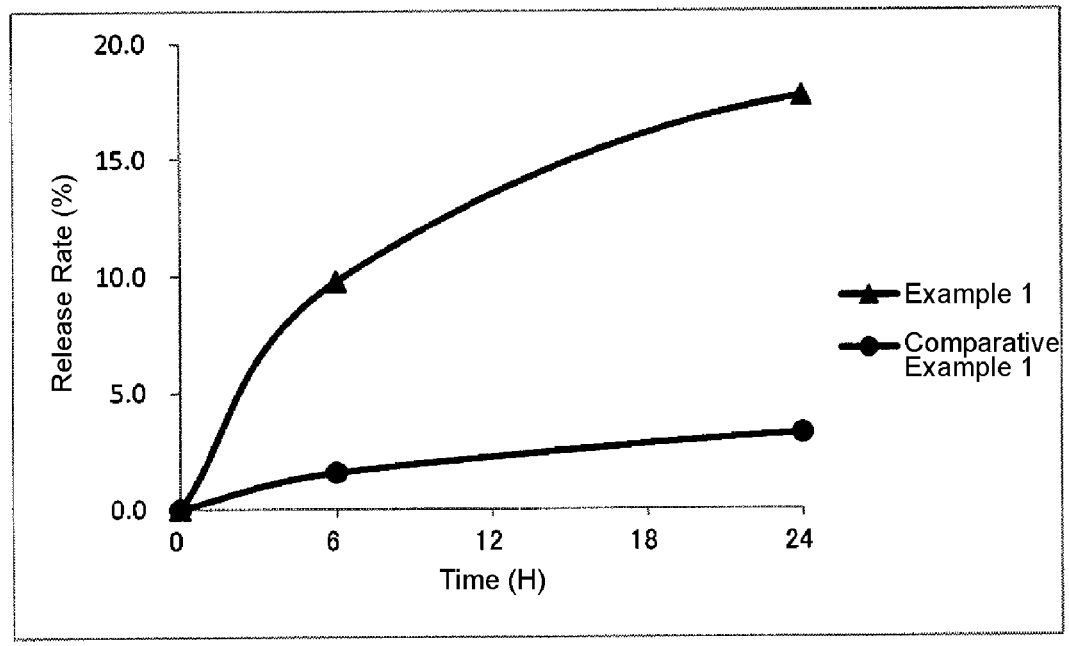
[Figure 2]
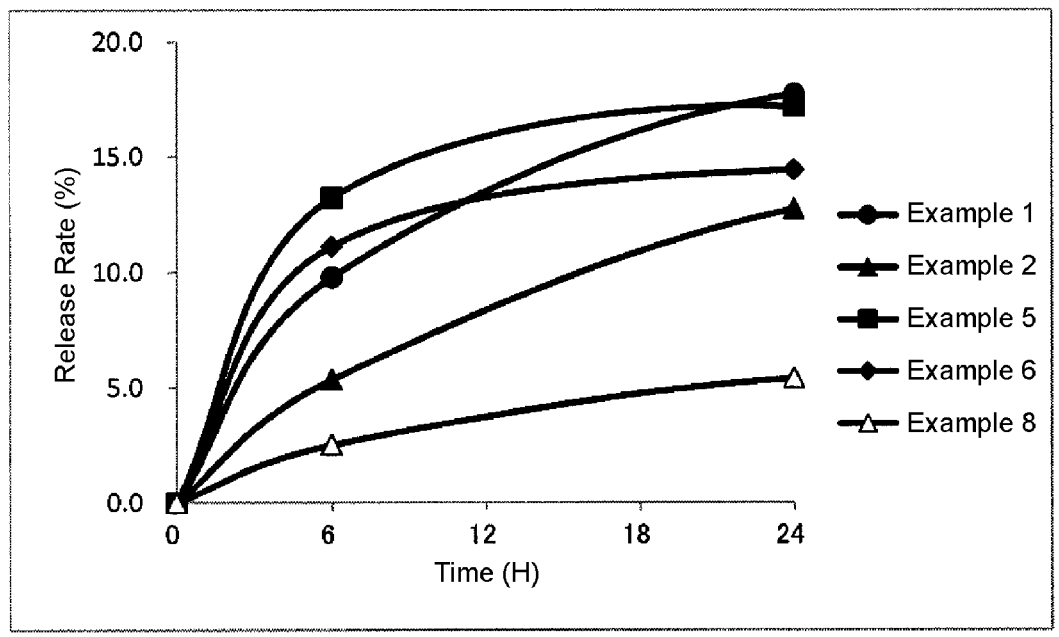

[Figure 3]
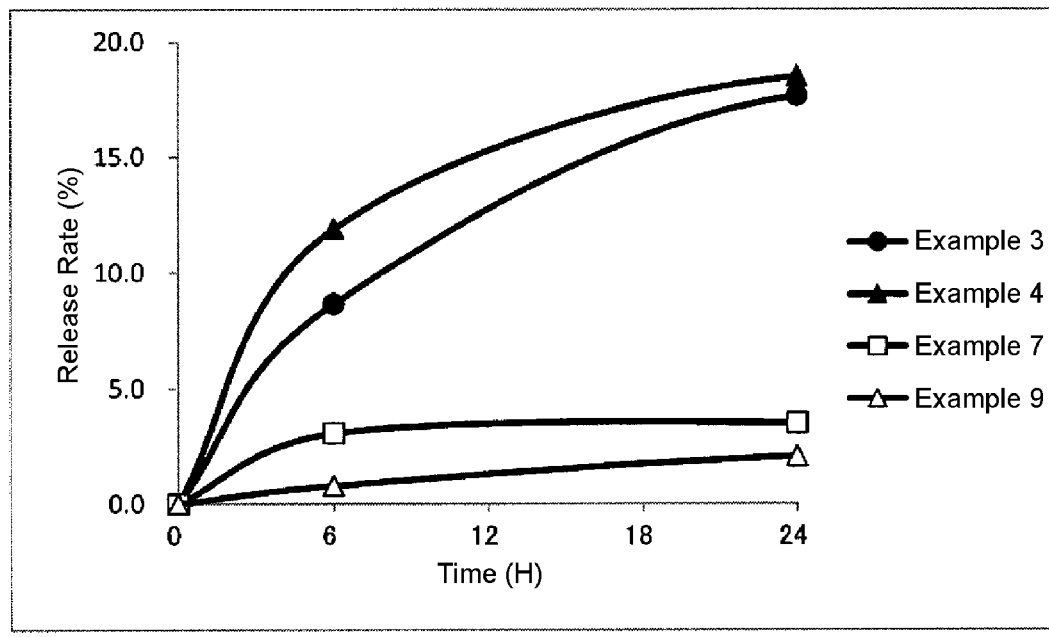
[Figure 4]
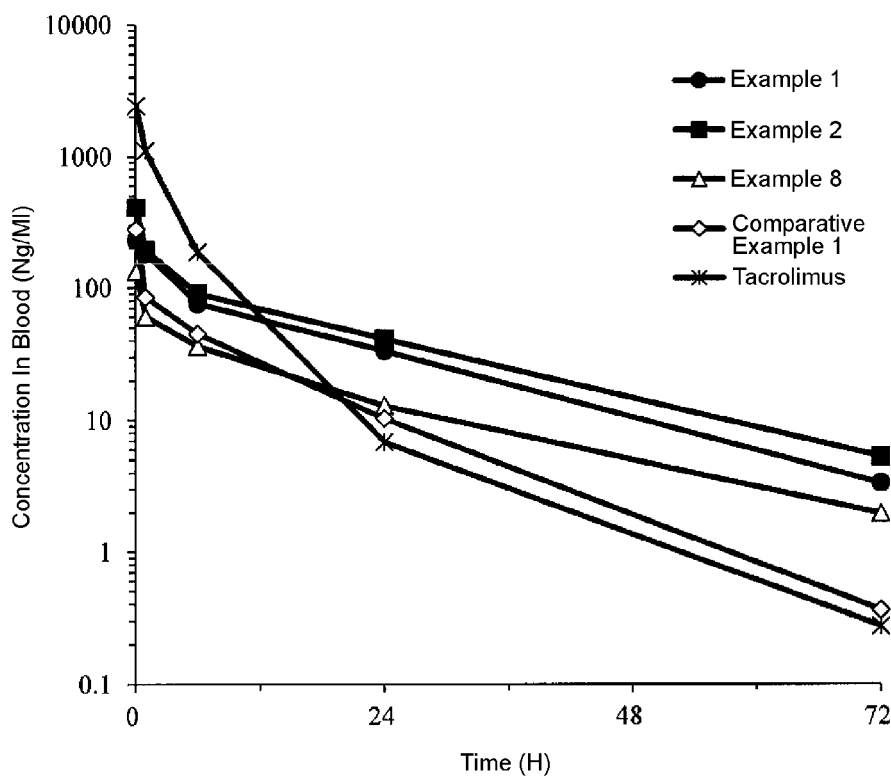

[Figure 5]
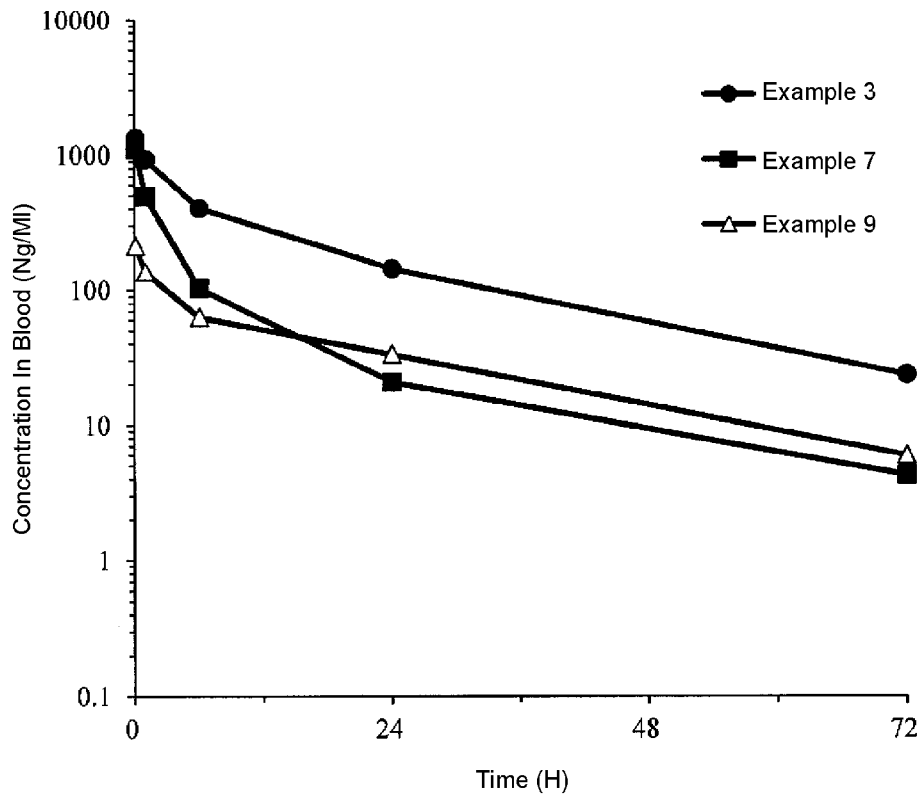
[Figure 6]
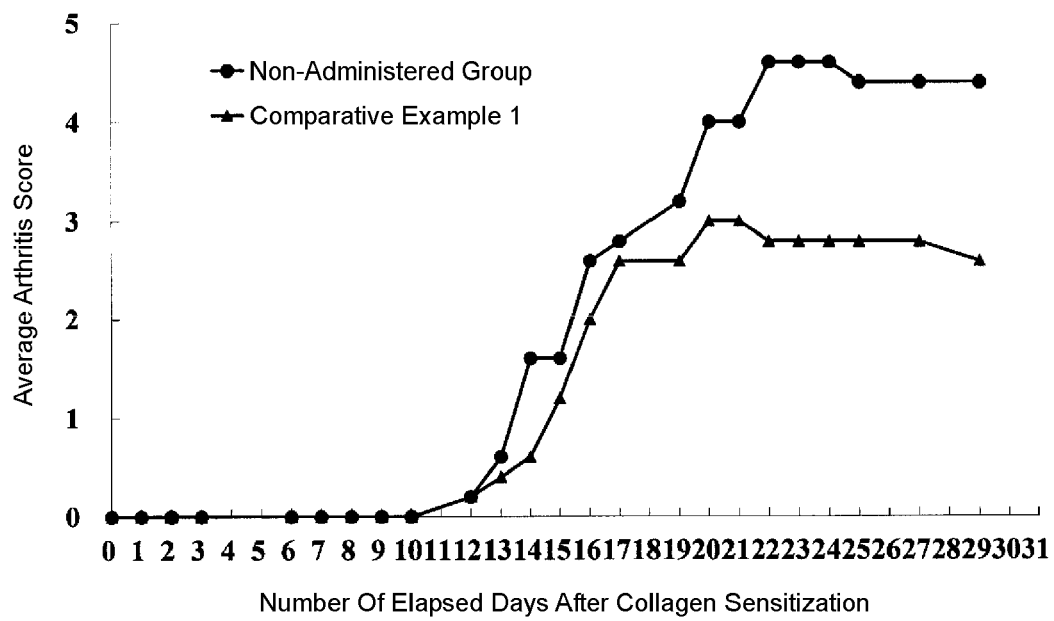

[Figure 7]
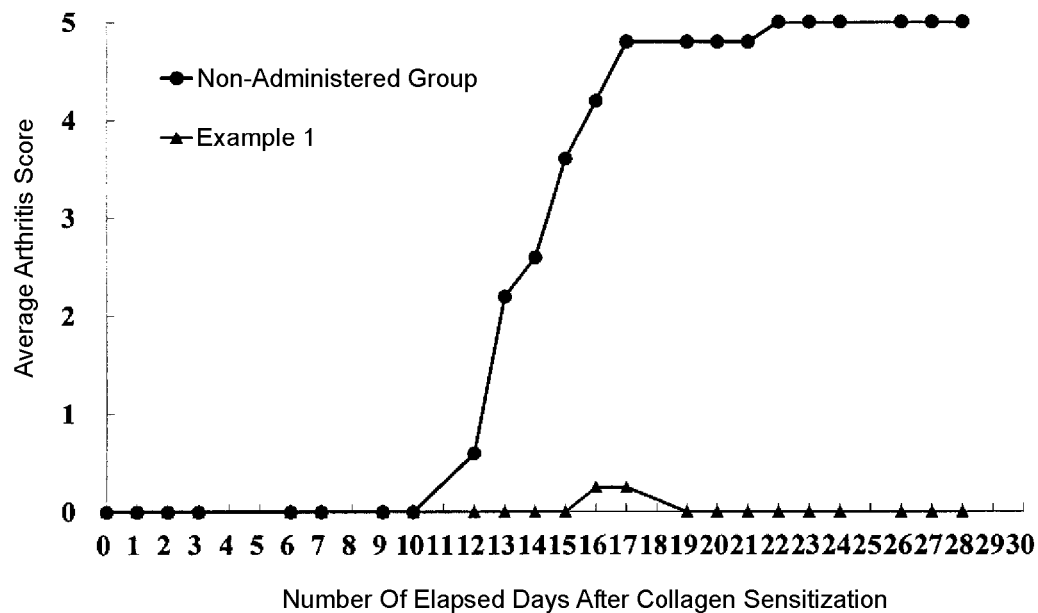
[Figure 8]
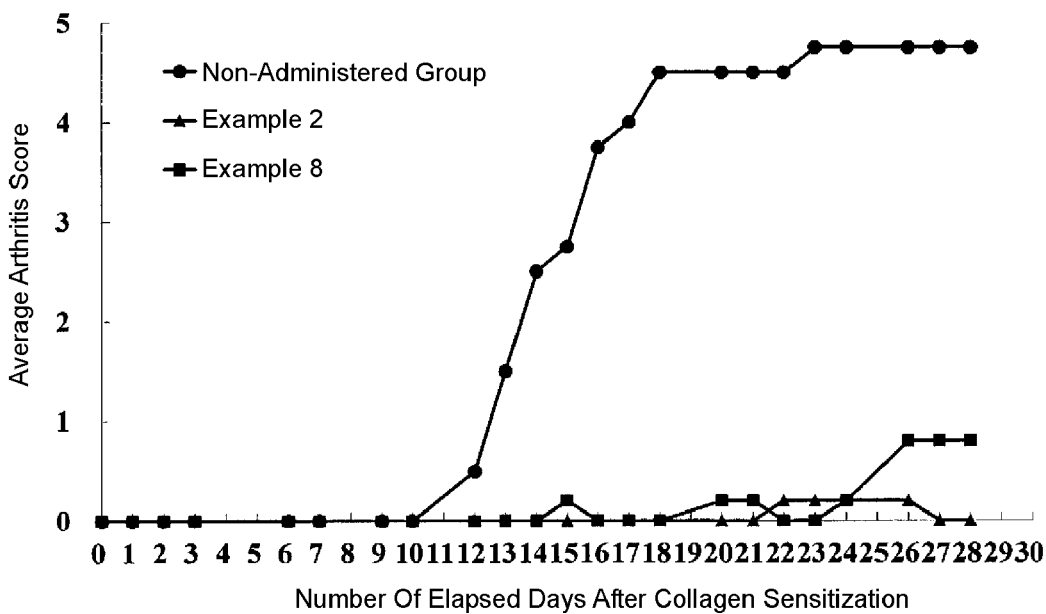

[Figure 9]
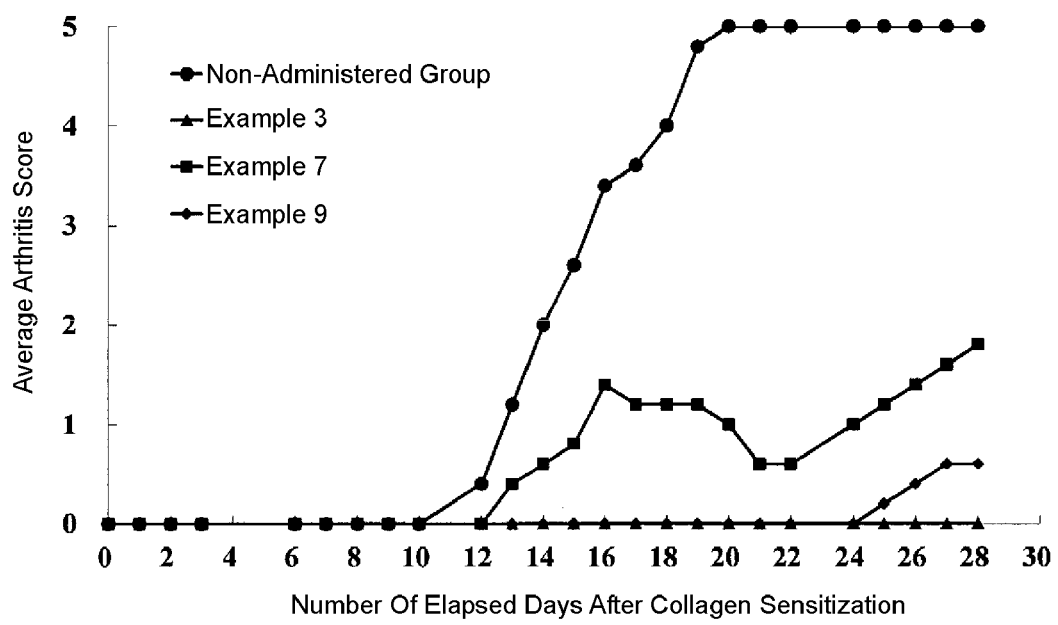

POLYMER DERIVATIVE OF MACROLIDE IMMUNOSUPPRESSANT

TECHNICAL FIELD

The present invention relates to polymeric derivatives of macrolide-based compounds, methods for preparing the polymeric derivatives, and use of the polymeric derivatives.

BACKGROUND ART

Macrolide-based compounds used for the present invention share common activity of having an affinity to FKBP type immunophilin and of inhibiting the enzymatic activity of peptidyl-prolyl isomerases and/or rotamases. Examples of the macrolide-based compounds include tricyclic compounds including rapamycin, tacrolimus (FK506), ascomycin, and the like.

It is described in, for example, Patent Literature 1, that macrolide-based compounds or pharmaceutically acceptable salts thereof have excellent immunosuppressive action, antibacterial activity, and other pharmacological activity, and therefore, those compounds are useful for the treatment and prevention of rejection to a transplant of an organ or a tissue, a graft-versus-host reaction, an autoimmune disease, an infectious disease, and the like.

Tacrolimus is generally used for the suppression of a rejection reaction after organ transplantation and for the treatment of a graft-versus-host disease after bone marrow transplantation, intractable active phase ulcerative colitis, and the like. However, tacrolimus is sparingly soluble in water (2.4 to 3.6 µM, room temperature) and has low bioavailability at the time of oral administration. Furthermore, since the therapeutic range of tacrolimus is narrow, and the inter-subject and intra-subject variation in the pharmacokinetics is large, tacrolimus is a drug for which control of the concentration in blood is difficult. Some known causative factors for the variation in the pharmacokinetics of tacrolimus include low solubility in water, individual differences in the expression level and the genotype of P-glycoprotein or drug metabolizing enzyme, CYP3A, in the alimentary canal mucosa, and the like (Non Patent Literatures 1 and 2).

One of main side effects of tacrolimus is renal toxicity and pancreatic toxicity. Renal toxicity is caused by the occurrence of decreases in the blood flow rate and the glomerular filtration rate resulting from the vasoconstrictor action on renal arterioles, and stagnation of nutritional supplementation to the tubular cells. Pancreatic toxicity is the onset of impaired glucose tolerance caused by suppression of the insulin production from pancreatic β cells mainly based on the inhibition of insulin mRNA transcription in pancreatic β cells. These toxicities are expressed dependently on the concentration of tacrolimus in blood plasma.

Regarding side effects of tacrolimus on the central nerve system, reversible posterior encephalopathy syndrome, hypertensive encephalopathy, and the like have been reported to occur in human subjects (0.1% to less than 0.5%, including post-marketing surveillance). Furthermore, it has been recognized in rats that intravenous administration of tacrolimus causes slight respiratory distress, a decrease in locomotor activity, a prone position, stereotyped behavior, and the like (Non Patent Literature 3).

It is known that when a polymer and a drug are coupled, the drug has increased water-solubility or improved pharmacokinetics in vivo, and as a result, excellent effects in practical use, such as enhanced efficacy, reduced side effects, and sustainability of efficacy, are obtained. The coupling modes for a polymer and a drug include a case in which a polymer and a drug are covalently bonded to each other, and a case in which a polymer and a drug are physically adsorbed to each other. A drug covalently bonded to a polymer is released from the polymer in vivo by means of a hydrolysis reaction or the like. Meanwhile, a drug physically adsorbed to a polymer does not depend on any chemical reaction such as a hydrolysis reaction, and the drug is slowly released from the polymer in vivo. In both cases, no enzyme is involved in the release of the drug from the polymer; however, it is considered that the difference in the coupling mode for the polymer and the drug brings about differences in the mechanism of drug release.

Patent Literature 2 and Patent Literature 3 describe polymeric derivatives obtainable from a drug and a copolymer including a polyethylene glycol and polyaspartic acid. In the polymeric derivatives described in Patent Literature 2 and Patent Literature 3, the copolymer and the drug are physically adsorbed to each other. Sustained release of the polymeric derivative is attributed to slow dissociation of the drug from the copolymer, and thus, drug efficacy is selectively exhibited at diseased areas, while side effects occur at a reduced level.

Patent Literature 4 discloses a method of obtaining a compound in which tacrolimus is physically adsorbed to a polymer including an alkyl-substituted polylactide (MPEG-hexPLA). However, there is no description with regard to the concentration in blood or with regard to tacrolimus migrating specifically to diseased areas.

In Non Patent Literature 4, a PEGylated tacrolimus obtained by chemically bonding tacrolimus to a PEG polymer has been reported. However, the PEGylated tacrolimus did not give an effect superior to or equal to the effect of tacrolimus in inflammatory disease model animals such as a mouse with adjuvant arthritis and a mouse with lupus nephritis.

In Non Patent Literature 5, micelles synthesized by physically adsorbing tacrolimus to a Poly (ethylene glycol) esters-Poly caprolactone (PEG-PCL) polymer have been reported. It has been found that the PEG-PCL tacrolimus micelles have superior inflammation ameliorating effects such as suppression of body weight reduction, suppression of shortening of the large intestine, and disappearance of hemorrhage in the large intestine or disappearance of crypt cells, compared to tacrolimus in a mouse with DSS-induced ulcerative colitis. However, since the PEG-PCL tacrolimus micelles are administered once a day successively for 12 days in order for the PEG-PCL tacrolimus micelles to exhibit inflammation ameliorating effects, it is speculated that when this compound is used, the concentration in blood may not be maintained for a long time period.

In Non Patent Literatures 6 and 7, micelles synthesized by physically adsorbing tacrolimus to a polymer including Poly caprolactone-b-poly(ethylene oxide) (PCL-b-PEO) have been reported. It is described that the PCL-b-PEO tacrolimus micelles are slowly taken into cells compared to tacrolimus. Furthermore, it is disclosed that when the PCL-b-PEO tacrolimus micelles were intravenously administered through the caudal vein at a dose of 5 mg/kg three times at an interval of 6 days, spontaneous motility of a sciatic nerve injury model rat was improved. However, since tacrolimus liberated from the PCL-b-PEO tacrolimus micelles highly accumulates in the brain, it is considered that the PCL-b-PEO tacrolimus micelles are specialized in the function as a neuroprotective agent, rather than the function as an immunosuppressant.

In Non Patent Literature 8, nanoparticles synthesized by physically adsorbing tacrolimus to a polymer including poly(lactic-co-glycolic acid) (PLGA) or pH-sensitive Eudragit P-4135F have been reported. These nanoparticles exhibit higher inflammation ameliorating effects than tacrolimus in mice with collagen-induced arthritis and DSS-induced colitis. However, since the nanoparticles should be administered once a day successively for 12 days in order for the nanoparticles to exhibit an inflammation ameliorating effect, it is speculated that when this compound is used, the concentration in blood may not be maintained for a long time period. Furthermore, the ameliorating action against BUN, serum creatinine, and creatinine clearance, which are indicators for nephropathy, are also not sufficient.

To this date, a preparation which shows high accumulability at diseased areas, shows markedly enhanced effectiveness and safety compared to tacrolimus, and has the concentration in blood maintained at a constant level without individual differences, whereby the control of the amount of administration depending on the blood kinetics (blood trough concentration) becomes unnecessary, has not yet been developed, and there is a demand for the development of such a preparation.

CITATION LIST

Patent Literature

Patent Literature 1: WO 93/005059 A
Patent Literature 2: WO 2003/000771 A
Patent Literature 3: WO 2004/082718 A
Patent Literature 4: WO 2013/157664 A Non Patent Literature Non Patent Literature 1: Transplantation, 1999, 67, p. 333-335
Non Patent Literature 2: Pharm. Res., 1998, 15, p. 1609-1613
Non Patent Literature 3: Materials on PROGRAPH capsules (0.5 mg, 1 mg, 5 mg) and PROGRAPH injectable solution (5 mg) of Fujisawa Pharmaceutical Co., Ltd. (currently Astellas Pharma Inc.), p. 53, Summary of application materials for department meeting deliberation and approval of June 2001
Non Patent Literature 4: Arch. Pharm. Res., 2011, 34, 1301-1310
Non Patent Literature 5: J. Biomed. Nanotechnol., 2013, 9, p. 147-157
Non Patent Literature 6: Drug. Deliv., 2000, 7, p. 139-145
Non Patent Literature 7: Biochim. Biophys. Acta, 1999, 1421, p. 32-38
Non Patent Literature 8: Int. J. Pharm., 2006, 316, p. 138-143

SUMMARY OF INVENTION

Technical Problem

An object of the present invention is to provide a novel immunosuppressant or a novel anti-inflammatory agent, which accumulates the drug at an inflammation site, exhibits a superior effect with a low amount of administration, has a long administration interval and reduces toxicity by maintaining the target concentration in blood.

Solution to Problem

The inventors of the present invention found that a polymeric derivative of tacrolimus, in which a polyethylene glycol segment and an alcoholic hydroxy group of tacrolimus are bonded to side-chain carboxy groups of a polyamino acid derivative, solves the problems of the present invention.

The present invention relates to the following [1] to [14].

[1] A polymeric derivative of tacrolimus, including a polyaspartic acid derivative, a polyethylene glycol segment, and tacrolimus,
wherein the polyethylene glycol segment and an alcoholic hydroxy group of tacrolimus are bonded to side-chain carboxy groups of the polyaspartic acid derivative.

[2] The polymeric derivative of tacrolimus according to [1], wherein the polymeric derivative is represented by the following General Formula (1):

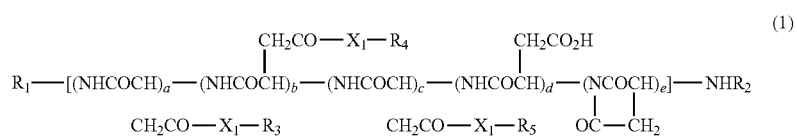

wherein $R_1$ represents a group selected from a group consisting of a hydrogen atom, a (C1-C8) alkyl group, and a polyethylene glycol segment; $R_2$ represents a group selected from a group consisting of a hydrogen atom, a (C1-C8) acyl group, and a (C1-C8) alkoxycarbonyl group; $R_3$ represents a residue of an alcoholic hydroxy group of tacrolimus; $R_4$ represents a polyethylene glycol segment; $R_5$ represents $-N(R_6)CONH(R_7)$ (wherein $R_6$ and $R_7$, which may be identical or different, each represent a (C3-C6) cyclic alkyl group or a (C1-C5) alkyl group which may be substituted with a tertiary amino group); $X_1$ represents a bond or a linking group; a and b each represent an integer from 1 to 299; c, d, and e each represent zero or an integer of 298 or less; a+b+c+d+e represents an integer from 2 to 300; and the order of arrangement of the various repeating units of the polyaspartic acid derivative is arbitrary.

[3] The polymeric derivative of tacrolimus according to [1], wherein the polymeric derivative is represented by the following General Formula (2):

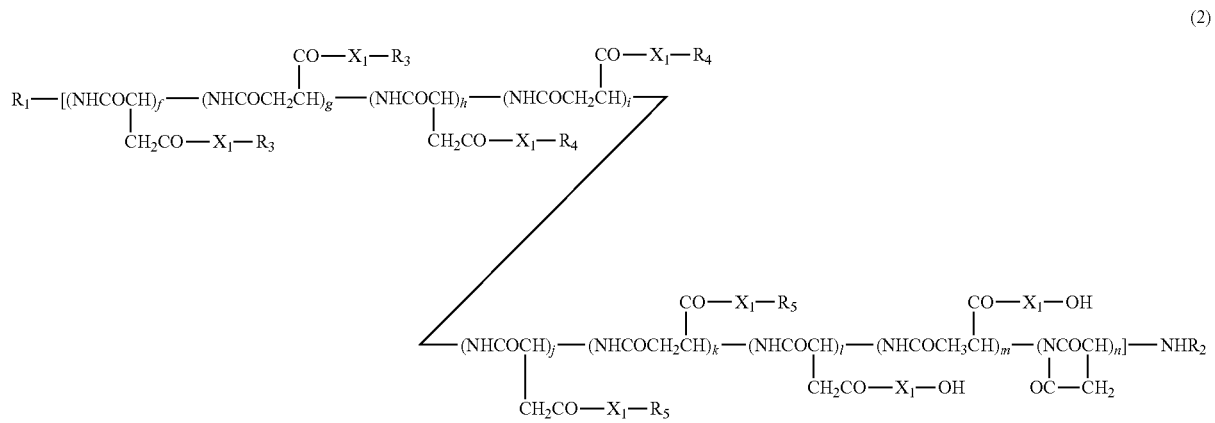
(2)

wherein $R_1$ represents a group selected from a group consisting of a hydrogen atom, a (C1-C8) alkyl group, and a polyethylene glycol segment; $R_2$ represents a group selected from a group consisting of a hydrogen atom, a (C1-C8) acyl group, and a (C1-C8) alkoxycarbonyl group; $R_3$ represents a residue of an alcoholic hydroxy group of tacrolimus; $R_4$ represents a polyethylene glycol segment; $R_5$ represents —N($R_6$)CONH ($R_7$) (wherein $R_6$ and $R_7$, which may be identical or different, each represent a (C3-C6) cyclic alkyl group or a (C1-C5) alkyl group which may be substituted with a tertiary amino group); $X_1$ represents a bond or a linking group; f, g, h, and i each represent zero or an integer of 299 or less; f+g and h+i each represent an integer from 1 to 299 or less; j, k, l, m, and n each represent zero or an integer of 298 or less; f+g+h+i+j+k+l+m+n represents an integer from 2 to 300; and the order of arrangement of the various repeating units of the polyaspartic acid derivative is arbitrary.

[4] The polymeric derivative of tacrolimus according to [2] or [3], wherein $X_1$ represents a bond.

[5] The polymeric derivative of tacrolimus according to [2] or [3], wherein $X_1$ represents an aspartic acid derivative.

[6] The polymeric derivative of tacrolimus according to [2] or [3], wherein $X_1$ is represented by the following General Formula (3) or General Formula (4):

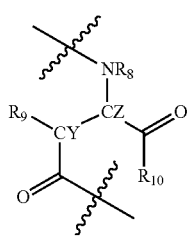
(3)

-continued

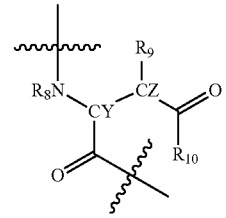
(4)

wherein $R_8$ and $R_9$ each independently represent a hydrogen atom or a (C1-C8) alkyl group; $R_{10}$ represents one or more groups selected from a group consisting of an amino group, a linear, branched or cyclic (C1-C20) alkylamino group which may have a substituent, a linear, branched or cyclic (C7-C20) aralkylamino group which may have a substituent, a (C5-C20) aromatic amino group which may have a substituent, and an amino acid residue having a protected carboxy group; and CY—CZ represents CH—CH or C=C (double bond).

[7] The polymeric derivative of tacrolimus according to [6], wherein $R_8$ and $R_9$ both represent a hydrogen atom; and CY—CZ represents CH—CH.

[8] The polymeric derivative of tacrolimus according to any one of [2] to [7], wherein the polyethylene glycol segment of $R_4$ is represented by the following General Formula (5):

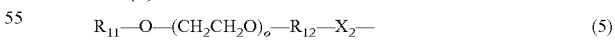
(5)

wherein $R_{11}$ represents a hydrogen atom, or a linear, branched or cyclic (C1-C6) alkyl group which may have a substituent; $R_{12}$ represents a (C2-C6) alkylene group; $X_2$ represents a functional group bondable to a side-chain carboxy group of the polyaspartic acid derivative; and o represents an integer from 5 to 11,500.

[9] The polymeric derivative of tacrolimus according to any one of [2] to [8], wherein $R_1$ represents a (C1-C6) alkyl group or a polyethylene glycol segment represented by the following General Formula (6):

(6)

wherein $R_{13}$ represents a hydrogen atom, or a linear, branched or cyclic (C1-C6) alkyl group which may have a substituent; $R_{14}$ represents a (C2-C6) alkylene group; and p represents an integer from 5 to 11,500.

[10] The polymeric derivative of tacrolimus according to [8] or [9], wherein $R_2$ represents a (C1-C6) acyl group; o represents an integer from 10 to 3,000; and (a+b+c+d+e) or (f+g+h+i+j+k+l+m+n) represents an integer from 4 to 250.

[11] The polymeric derivative of tacrolimus according to [8] or [9], wherein $R_2$ represents a (C1-C3) acyl group; o represents an integer from 20 to 1,500; and (a+b+c+d+e) or (f+g+h+i+j+k+l+m+n) represents an integer from 8 to 200.

[12] The polymeric derivative of tacrolimus according to any one of [2] to [11], wherein $R_1$ represents a methyl group, and $R_2$ represents an acetyl group.

[13] A method for producing the polymeric derivative of tacrolimus according to any one of [1] to [12], wherein an alcoholic hydroxy group of tacrolimus and a polyethylene glycol segment are bonded to side-chain carboxy groups of a polyaspartic acid derivative via an ester bond, an amide bond, and/or a thioester bond using a dehydration condensing agent in an organic solvent.

[14] A macrolide immunosuppressant including the polymeric derivative of tacrolimus according to any one of [1] to [12] as an active ingredient.

Advantageous Effects of Invention

The polymeric derivative of tacrolimus of the present invention has a feature that a polyethylene glycol segment and an alcoholic hydroxy group of tacrolimus are bonded, directly or via a linking group, to side-chain carboxy groups of a polyaspartic acid derivative. This polymeric derivative is stable in vivo, may release tacrolimus slowly in an enzyme-independent manner, and exhibits excellent blood retentivity. Thus, the polymeric derivative exhibits an excellent therapeutic effect with a low amount of administration. Furthermore, since the polymeric derivative is capable of enzyme-independent release of a physiologically active substance and maintenance of the concentration in blood, control of the amount of administration depending on the blood kinetics (blood trough concentration) becomes unnecessary, and safety is expected to be markedly enhanced.

BRIEF DESCRIPTION OF DRAWINGS

FIG. 1 shows the proportions of the amount of released tacrolimus with respect to the total amount of tacrolimus of Example 1 and Comparative Example 1 obtained in Test Example 1.

FIG. 2 shows the proportions of the amount of released tacrolimus with respect to the total amount of tacrolimus of Examples 1, 2, 5, 6, and 8 obtained in Test Example 1.

FIG. 3 shows the proportions of the amount of released tacrolimus with respect to the total amount of tacrolimus of Examples 3, 4, 7, and 9 obtained in Test Example 1.

FIG. 4 shows the profiles of the blood concentration in rats of Examples 1, 2, and 8, Comparative Example 1 and tacrolimus obtained in Test Example 2.

FIG. 5 shows the profiles of the blood concentration in rats of Examples 3, 7, and 9 obtained in Test Example 3.

FIG. 6 shows an anti-inflammatory effect of Comparative Example 1 against rat collagen-induced arthritis, as obtained in Test Example 4.

FIG. 7 shows an anti-inflammatory effect of Example 1 against rat collagen-induced arthritis, as obtained in Test Example 4.

FIG. 8 shows an anti-inflammatory effect of Examples 2 and 8 against rat collagen-induced arthritis, as obtained in Test Example 4.

FIG. 9 shows an anti-inflammatory effect of Examples 3, 7, and 9 against rat collagen-induced arthritis, as obtained in Test Example 4.

DESCRIPTION OF EMBODIMENTS

The polymeric derivative of tacrolimus of the present invention has a feature that a polyethylene glycol segment and an alcoholic hydroxy group of tacrolimus are bonded, directly or via a linking group, to side-chain carboxy groups of a polyaspartic acid derivative. The details will be explained below.

The polymeric derivative of tacrolimus of the present invention is a polymer compound having a polyaspartic acid derivative containing a plurality of units as the polymer main chain structure. That is, the polymeric derivative of tacrolimus of the present invention is a polymerized derivative which has a polyaspartic acid derivative having a plurality of side-chain carboxy groups as a main chain structure of the polymer carrier, and in which the side-chain carboxy groups are chemically functionalized by a polyethylene glycol segment and a macrolide immunosuppressant.

The polyaspartic acid derivative having side-chain carboxy groups, which is used for the polymeric derivative of tacrolimus of the present invention, may be an α-amide bond type polymer, may be an amide bond type polymer with side-chain carboxy groups, may be a β-amide bond type polymer, or may be a mixture thereof. The polyaspartic acid derivative is preferably an α-amide bond type polymer or a mixture of an α-amide bond type polymer and a β-amide bond type polymer. The polymeric derivative of tacrolimus of the present invention has, for example, a structure represented by the following General Formula (1) or General Formula (2).

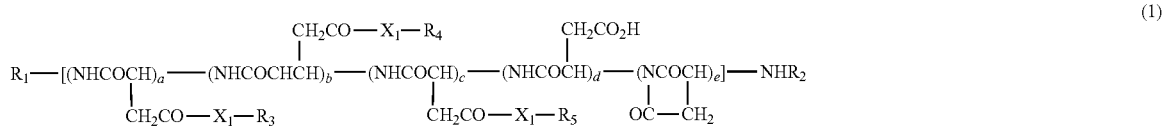
(1)

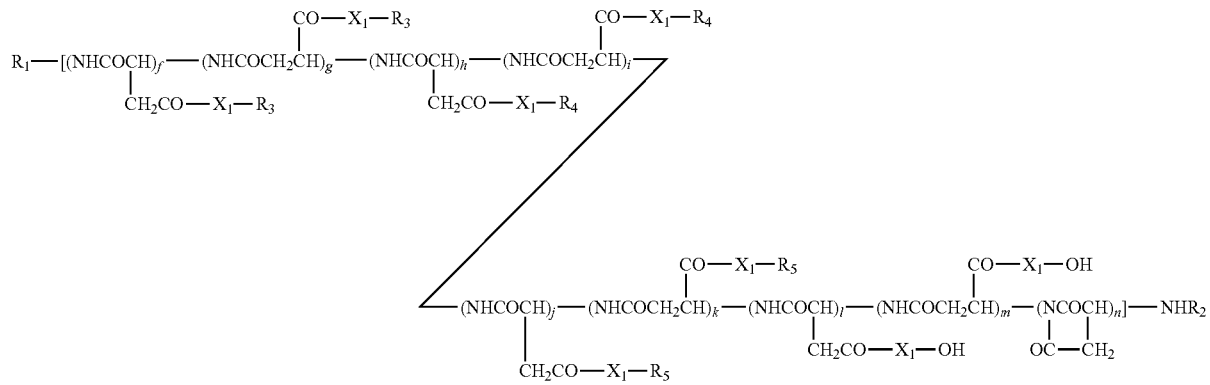

(2)

In General Formulae (1) and (2), $R_1$ represents a group selected from a group consisting of a hydrogen atom, a (C1-C8) alkyl group, and a polyethylene glycol segment; $R_2$ represents a group selected from a group consisting of a hydrogen atom, a (C1-C8) acyl group, and a (C1-C8) alkoxycarbonyl group; $R_3$ represents a residue of an alcoholic hydroxy group of tacrolimus; $R_4$ represents a polyethylene glycol segment; $R_5$ represents —N($R_6$)CONH($R_7$) (wherein $R_6$ and $R_7$, which may be identical or different, each represent a (C3-C6) cyclic alkyl group or a (C1-C5) alkyl group which may be substituted with a tertiary amino group); and $X_1$ represents a bond or a linking group.

In General Formula (1) described above, a, b, c, d, and e all represent average values. a and b each represent an integer from 1 to 299. Meanwhile, c, d, and e each represent zero or an integer of 298 or less, and a+b+c+d+e represents an integer from 2 to 300.

In General Formula (2) described above, f, g, h, i, j, k, l, m, and n all represent average values. f, g, h, and i each represent zero or an integer of 299 or less. Meanwhile, f+g and h+i each represent an integer from 1 to 299, and j, k, l, m, and n each represent zero or an integer of 298 or less, while f+g+h+i+j+k+l+m+n represents an integer from 2 to 300.

Meanwhile, the order of arrangement of the various repeating units is not particularly limited, and the repeating units may be randomly disposed. The order of arrangement is not limited to the orders described in General Formula (1) and General Formula (2).

Regarding the terminal groups of the polyaspartic acid derivative, both the N-terminal group ($R_2$ in General Formula (1) and General Formula (2)) and the C-terminal group ($R_1$ in General Formula (1) and General Formula (2)) are not particularly limited, and the terminal groups may be an unprotected free amino group and a free carboxylic acid, or salts thereof. The terminal groups may also be appropriate modified forms of the N-terminal group and the C-terminal group.

Examples of the modified form of the N-terminal group of the polyaspartic acid derivative include an acyl amide type modified form, an alkoxycarbonylamide type modified form (urethane type modified form), and an alkylaminocarbonylamide type modified form (urea type modified form). Examples of the modified form of $R_2$, which is the N-terminal group in General Formula (1) and General Formula (2), include an acyl amide type modified form and an alkoxycarbonylamide type modified form (urethane type modified form).

Meanwhile, examples of the modified form of the C-terminal group of the polyaspartic acid derivative include an ester type modified form, an amide type modified form, and a thioester type modified form. The modified form of $R_1$, which is the C-terminal group in General Formula (1) and General Formula (2), is an amide type modified form.

The modifying group for the N-terminal group and the C-terminal group of the polyaspartic acid derivative may be any arbitrary modifying group. Preferred examples include terminal modifying groups such as a linear, branched or cyclic (C1-C6) alkyl group which may have a substituent, a (C6-C18) aromatic group which may have a substituent, and a (C7-C20) aralkyl group which may have a substituent, all of which may be placed via an appropriate linking group that is bonded to the N-terminal group and the C-terminal group. Alternatively, the modifying group may be a polyethylene glycol segment capable of imparting water-solubility, and the modifying group may be a terminal modifying group linked via an appropriate linking group that is bonded to the N-terminal group and the C-terminal group.

That is, the N-terminal group is preferably an appropriate acyl amide type modified form or an alkoxycarbonylamide type modified form (urethane type modified form), and it is preferable that the N-terminal group is a linear, branched or cyclic (C1-C8) alkyl group which may have a substituent, a (C6-C18) aromatic group which may have a substituent, or a (C7-C20) aralkyl group which may have a substituent, all of which are linked via a carbonyl group or a carbonyloxy group.

Meanwhile, the C-terminal group is preferably an appropriate amide type substituent or an ester type substituent, and it is preferable that the C-terminal group is a linear, branched or cyclic (C1-C8) alkyl group which may have a substituent, a (C6-C18) aromatic group which may have a substituent, a (C7-C20) aralkyl group which may have a substituent, or a polyethylene glycol segment, all of which are linked via an amide group or an ester group.

The polyethylene glycol segment of $R_1$ of General Formulae (1) and (2), which is the C-terminal group, is a segment having a repeating structure of an ethyleneoxy group: ($CH_2CH_2O$) unit. The polyethylene glycol segment preferably has a segment structure including a polyethylene glycol chain having an average value of the repetition number of the ethyleneoxy group unit (degree of polymerization) of 5 to 11,500 units, more preferably having a degree of polymerization of 10 to 3,000 units, and particularly preferably having a degree of polymerization of 20 to 1,500 units. That is, the polyethylene glycol segment has a molecular weight of 200 daltons to 500 kilodaltons as a polyethylene glycol-equivalent average molecular weight. A preferred molecular weight is 500 daltons to 150 kilodaltons, and a more preferred molecular weight is 1,000 daltons to 70 kilodaltons. Particularly, it is preferable that the molecular weight is 1,000 daltons to 50 kilodaltons.

A structure example of the polyethylene glycol segment of $R_1$ may be a structure represented by the following General Formula (6). That is, it is preferable that the polyethylene glycol segment has a structure in which an oxygen atom of an ethyleneoxy group unit and a (C1-C8) alkylene group are ether-bonded.

$$R_{13}-O-(CH_2CH_2O)_p-R_{14}- \quad (6)$$

p of General Formula (6) is an average value and represents an integer of about 5 to 11,500, preferably about 10 to 3,000, and particularly preferably about 20 to 1,500.

The terminal group ($R_{13}$) of the polyethylene glycol segment of $R_1$ is not particularly limited, and examples include a hydrogen atom, a linear, branched or cyclic (C1-C6) alkyl group which may have a substituent, a (C2-C6) alkynyl group which may have a substituent, and a (C7-C20) aralkyl group which may have a substituent. Examples of the substituent for the alkyl group, alkynyl group, and aralkyl group include a hydroxy group, an amino group, a formyl group, and a carboxy group.

In regard to the terminal groups of the polyethylene glycol segment of $R_1$, examples of the linear alkyl group which may have a substituent include a methyl group, an ethyl group, a n-propyl group, a n-butyl group, a n-pentyl group, and a n-hexyl group. Examples of the branched alkyl group which may have a substituent include an isopropyl group, an isobutyl group, a t-butyl group, an isopentyl group, a 2-methylbutyl group, a neopentyl group, a 1-ethylpropyl group, a 4-methylpentyl group, a 3-methylpentyl group, a 2-methylpentyl group, a 1-methylpentyl group, a 3,3-dimethylbutyl group, a 2,2-dimethylbutyl group, a 1,1-dimethylbutyl group, a 1,2-dimethylbutyl group, a 1,3-dimethylbutyl group, a 2,3-dimethylbutyl group, and a 2-ethylbutyl group. Examples of the cyclic alkyl group which may have a substituent include a cyclopropyl group, a cyclobutyl group, a cyclopentyl group, and a cyclohexyl group.

In regard to the terminal groups of the polyethylene glycol segment of $R_1$, examples of the substituent that may be carried by the linear, branched or cyclic alkyl group include a thiol group, a hydroxy group, a halogen atom, a nitro group, a cyano group, an alkylthio group, a carbocyclic or heterocyclic aryl group, an arylthio group, an alkylsulfinyl group, an arylsulfinyl group, an alkylsulfonyl group, a sulfamoyl group, an alkoxy group, an aryloxy group, an acyloxy group, an alkoxycarbonyloxy group, a carbamoyloxy group, a substituted or unsubstituted amino group, an acylamino group, an alkoxycarbonylamino group, a ureido group, a sulfonylamino group, a sulfamoylamino group, a formyl group, an acyl group, a carboxy group, an alkoxycarbonyl group, a carbamoyl group, and a silyl group.

In regard to the terminal groups of the polyethylene glycol segment of $R_1$, examples of the (C2-C6) alkynyl group which may have a substituent include a 2-propynyl group, a 3-butynyl group, a 4-heptynyl group, and a 5-hexynyl group.

In regard to the terminal groups of the polyethylene glycol segment of $R_1$, the (C7-C20) aralkyl group which may have a substituent is a linear or branched alkyl group having any one hydrogen atom substituted by an aryl group. Examples include a benzyl group, a 2-phenylethyl group, a 4-phenylbutyl group, a 3-phenylbutyl group, a 5-phenylpentyl group, a 6-phenylhexyl group, and an 8-phenyloctyl group. Preferred examples include a benzyl group, a 4-phenylbutyl group, and an 8-phenyloctyl group.

The terminal group ($R_{14}$) on the side of linkage to the polyaspartic acid main chain in the polyethylene glycol segment of $R_1$ is not particularly limited as long as it is a linking group adequate for the polyaspartic acid derivative. Preferably, the terminal group is a (C1-C8) alkylene group which may have a substituent. Examples include a methylene group, an ethylene group, a trimethylene group, a butylene group, a hexamethylene group, and an octamethylene group. $R_{14}$ of General Formula (6) is preferably a trimethylene group.

$R_2$ of General Formula (1) and General Formula (2) is a substituent selected from a group consisting of a hydrogen atom, a (C1-C8) acyl group, and a (C1-C8) alkoxycarbonyl group.

The (C1-C8) acyl group is a linear, branched or cyclic (C1-C8) acyl group. Examples include a formyl group, an acetyl group, a propionyl group, a butyroyl group, a cyclopropylcarbonyl group, and a cyclopentanecarbonyl group.

The (C1-C8) alkoxycarbonyl group is a linear, branched or cyclic (C1-C8) alkoxycarbonyl group. Examples include a methoxycarbonyl group, an ethoxycarbonyl group, a propoxycarbonyl group, an isopropoxycarbonyl group, a n-butoxycarbonyl group, a t-butoxycarbonyl group, a pentoxycarbonyl group, a hexyloxycarbonyl group, a cyclopropoxycarbonyl group, a cyclopentyloxycarbonyl group, and a cyclohexyloxycarbonyl group.

According to the present invention, the residue of an alcoholic hydroxy group of tacrolimus of $R_3$ of General Formula (1) and General Formula (2) refers to a tacrolimus in which an alcoholic hydroxy group of tacrolimus is ester-bonded, directly or via a linking group, to a side-chain carboxy group of a polyaspartic acid derivative.

Tacrolimus is represented by the following Formula (I). There are a large number of alcoholic hydroxy groups of tacrolimus; however, the position of substitution is not limited as long as the hydroxy group is an alcoholic hydroxy group.

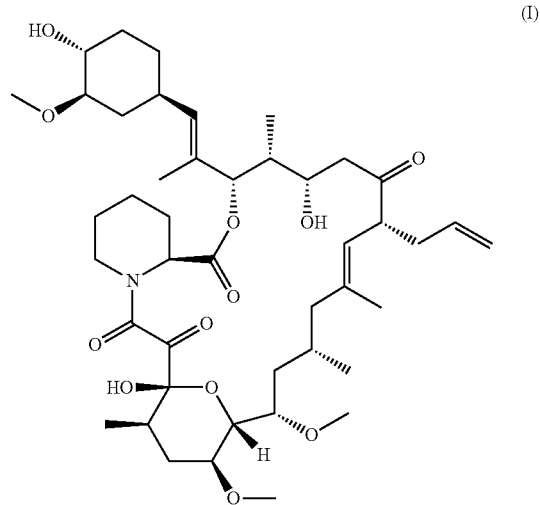 [SMILES: C=CC[C@@H]1/C=C(\C)C[C@H](C)C[C@H](OC)[C@H]2O[C@@](O)(C(=O)C(=O)N3CCCC[C@H]3C(=O)O[C@H](/C(C)=C/[C@@H]3CC[C@@H](O)[C@H](OC)C3)[C@H](C)[C@@H](O)CC1=O)[C@H](C)C[C@@H]2OC]

(I)

The polyethylene glycol segment bonded to a side-chain carboxy group of a polyaspartic acid derivative directly or via a linking group, has a repeating structure of an ethyleneoxy group unit, similarly to the polyethylene glycol segment of $R_1$ of General Formula (1) and General Formula (2), and the degree of polymerization and the average molecular weight are also the same as those of the polyethylene glycol segment of $R_1$. $R_4$ of General Formula (1) and General Formula (2) represents a polyethylene glycol segment that is bonded, directly or via a linking group, to a side-chain carboxy group of a polyaspartic acid derivative.

The polyethylene glycol segment bonded to a side-chain carboxy group of a polyaspartic acid derivative directly or via a linking group, is such that 1 to 200 units are bonded to one molecule of the polyaspartic acid derivative. That is, the polymeric derivative of tacrolimus has a plurality of units of the polyethylene glycol segment. Preferably, the polymeric derivative of tacrolimus has 1 to 150 units, and more preferably 1 to 100 units, of the polyethylene glycol segment.

An example of $R_4$ for General Formula (1) and General Formula (2) may be a structure represented by the following General Formula (5).

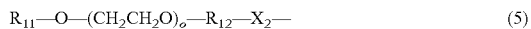

$$R_{11}\text{—O—}(CH_2CH_2O)_o\text{—}R_{12}\text{—}X_2\text{—} \quad (5)$$

In General Formula (5), $R_{11}$ represents a group selected from a group consisting of a hydrogen atom, a linear, branched or cyclic (C1-C6) alkyl group which may have a substituent, a (C2-C6) alkynyl group which may have a substituent, and a (C7-C20) aralkyl group which may have a substituent. $R_{12}$ represents a (C2-C6) alkylene group. $X_2$ represents a functional group that is bondable to a side-chain carboxy group of the polyaspartic acid derivative. o is an average value and represents an integer from 5 to 11,500, preferably 10 to 3,000, and particularly preferably 20 to 1,500.

$R_{11}$ is not particularly limited, and examples include a hydrogen atom, a linear, branched or cyclic (C1-C6) alkyl group which may have a substituent, a (C2-C6) alkynyl group which may have a substituent, and a (C7-C20) aralkyl group which may have a substituent. Examples of the substituent that may be carried by the alkyl group, alkynyl group, and aralkyl group include a hydroxy group, an amino group, a formyl group, and a carboxy group.

Examples of the linear alkyl group which may have a substituent for $R_{11}$ include a methyl group, an ethyl group, a n-propyl group, a n-butyl group, a n-pentyl group, and a n-hexyl group. Examples of the branched alkyl group which may have a substituent include an isopropyl group, an isobutyl group, a t-butyl group, an isopentyl group, a 2-methylbutyl group, a neopentyl group, a 1-ethylpropyl group, a 4-methylpentyl group, a 3-methylpentyl group, a 2-methylpentyl group, a 1-methylpentyl group, a 3,3-dimethylbutyl group, a 2,2-dimethylbutyl group, a 1,1-dimethylbutyl group, a 1,2-dimethylbutyl group, a 1,3-dimethylbutyl group, a 2,3-dimethylbutyl group, and a 2-ethylbutyl group. Examples of the cyclic alkyl group which may have a substituent include a cyclopropyl group, a cyclobutyl group, a cyclopentyl group, and a cyclohexyl group.

In regard to one of the terminal groups of the polyethylene glycol segment of $R_4$, examples of the substituent which may be carried by the linear, branched or cyclic alkyl group include a thiol group, a hydroxy group, a halogen atom, a nitro group, a cyano group, an alkylthio group, a carbocyclic or heterocyclic aryl group, an arylthio group, an alkylsulfinyl group, an arylsulfinyl group, an alkylsulfonyl group, a sulfamoyl group, an alkoxy group, an aryloxy group, an acyloxy group, an alkoxycarbonyloxy group, a carbamoyloxy group, a substituted or unsubstituted amino group, an acylamino group, an alkoxycarbonylamino group, a ureido group, a sulfonylamino group, a sulfamoylamino group, a formyl group, an acyl group, a carboxy group, an alkoxycarbonyl group, a carbamoyl group, and a silyl group.

In regard to one of the terminal groups of the polyethylene glycol segment of $R_4$, examples of the (C2-C6) alkynyl group which may have a substituent include a 2-propynyl group, a 3-butynyl group, a 4-heptynyl group, and a 5-hexynyl group.

In regard to one of the terminal groups of the polyethylene glycol segment of $R_4$, the (C7-C20) aralkyl group which may have a substituent is a linear or branched alkyl group which may have any one hydrogen atom substituted by an aryl group. Examples include a benzyloxy group, a 2-phenylethyl group, a 4-phenylbutyl group, a 3-phenylbutyl group, a 5-phenylpentyl group, a 6-phenylhexyl group, and an 8-phenyloctyl group. Preferred examples include a benzyl group, a 4-phenylbutyl group, and an 8-phenyloctyl group.

According to the present invention, $R_{11}$ is preferably a hydrogen atom or a linear, branched or cyclic (C1-C6) alkyl group which may have a substituent.

The terminal group ($R_{12}$) of $R_4$ on the side of linkage to a side-chain carboxy group of the polyaspartic acid derivative is not particularly limited as long as it is a functional group that is bondable to a side-chain carboxy group of the polyaspartic acid derivative mentioned above. According to the present invention, the terminal group is a (C2-C6) alkylene group, and examples include an ethylene group, a trimethylene group, and a butylene group, while a trimethylene group is particularly preferred.

$X_2$ of General Formula (5) is not particularly limited as long as it is a functional group that is bondable to a side-chain carboxy group of the polyaspartic acid derivative; however, according to the present invention, $X_2$ is preferably —NH—, —O—, or —S—.

$R_5$ of General Formula (1) and General Formula (2) may adopt —N($R_6$)CONH($R_7$). Here, $R_6$ and $R_7$, which may be identical or different, each represent a (C3-C6) cyclic alkyl group or a (C1-C5) alkyl group which may be substituted with a tertiary amino group.

Examples of the cyclic (C3-C6) alkyl group include a cyclohexyl group.

Examples of the (C1-C5) alkyl group which may be substituted with a tertiary amino group include an ethyl group, an isopropyl group, and a 3-dimethylaminopropyl group.

Examples of the tertiary amino group for the (C1-C5) alkyl group which may be substituted with a tertiary amino group include a dimethylamino group and a diethylamino group.

According to the present invention, the residue of an alcoholic hydroxy group of tacrolimus, the polyethylene glycol segment, and $R_5$ of General Formula (1) and General Formula (2) are respectively bonded to side-chain carboxy groups of a polyaspartic acid derivative via $X_1$ of General Formula (1) and General Formula (2). $X_1$ in General Formula (1) and General Formula (2) may be a linking group that links $R_3$, $R_4$, or $R_5$ to a side-chain carbonyl group of the polyaspartic acid main chain, or may be merely a bond. In a case in which $X_1$ is a linking group, the linking group is not particularly limited as long as the linking group has, at the two terminals, functional groups that may be respectively bonded to a bondable functional group of $R_3$, $R_4$ and $R_5$, and to a side-chain carboxy group of the polyaspartic acid derivative.

In a case in which $X_1$ is a linking group, the terminal bondable functional group on the side of $R_3$, $R_4$ and $R_5$ is preferably a carboxy group, an oxycarboxy group, or an aminocarboxy group. Since $R_3$, $R_4$ and $R_5$ have an amino group, a hydroxy group, and/or a thiol group in the molecule, each of these bondable functional groups forms an amide bond, an ester bond, a thioester bond, a urethane bond, a carbonate bond, and a urea bond with the amino group, hydroxy group, and/or thiol group.

The other terminal bondable functional group of $X_1$ on the side of the side-chain carboxy group is preferably an amino group, a hydroxy group, or a thiol group. Each of these bondable functional groups may form an amide bond, an ester bond, or a thioester bond with a side-chain carboxy group.

That is, $X_1$ is preferably a (C1-C8) alkylene group or alkenylene group which may have a substituent, the alkylene group or alkenylene group having a carboxy group, an oxycarboxy group or an aminocarboxy group as one terminal group and having an amino group, a hydroxy group, or a thiol group as the other terminal group.

In a case in which $X_1$ is a linking group, specific examples include the groups described in the table given below; however, the examples of the linking group are not limited to these as long as the linking group does not affect the synthesis or performance of the polymeric derivative of the present invention. $X_1$ in all cases forms an amide bond, an ester bond, or a thioester bond with a side-chain carboxy group.

TABLE 1

| Bonding with $R_3$, $R_4$, and/or $R_5$ | $X_1$ ($R_3$, $R_4$, or $R_5$ side → side-chain carboxy group side) |
|---|---|
| Amide bond, ester bond, or thioester bond | —CO—$(CH_2)_y$—NH—<br>—CO—$(CH_2)_y$—O—<br>—CO—$(CH_2)_y$—S— |
| Urea bond or urethane bond | —CONH—$(CH_2)_y$—HN—<br>—CONH—$(CH_2)_y$—O—<br>—CONH—$(CH_2)_y$—S— |
| Carbonate bond or urethane bond | —COO—$(CH_2)_y$—HN—<br>—COO—$(CH_2)_y$—O—<br>—COO—$(CH_2)_y$—S— |

Remark 1) y in the table represents an integer from 1 to 8 in all cases.
Remark 2) Hereinafter, $X_1$ is described as follows: $R_3$, $R_4$ or $R_5$ side → side-chain carboxy group side.

The alkylene group of $X_1$ may have one of its hydrogen atoms modified by an appropriate substituent. Examples of the substituent include a hydroxy group, an amino group, a halogen atom, a (C1-C8) alkyl group, a (C1-C8) alkylcarbonylalkoxy group, a (C1-C8) alkylcarbonylamide group, a (C1-C8) alkylcarbonylalkylamide group, a (C1-C8) alkylaryl group, a (C1-C8) alkoxy group, a (C1-C8) alkylamino group, a (C1-C8) acylamide group, and a (C1-C8) alkoxycarbonylamino group.

$X_1$ is preferably —CO—$(CH_2)_y$—NH— or —CO—$(CH_2)_y$—O—. Particularly preferably, $X_1$ is —CO—$(CH_2)_y$—NH—, which has a carboxy group that may form an amide bond, an ester bond or a thioester bond with $R_3$, $R_4$ or $R_5$, and also has an amino group that may form an amide bond with the side-chain carboxy group.

y in $X_1$ is preferably 1 to 6, and more preferably 1, 2, 3, or 5. The most preferred example of $X_1$ is —CO—$(CH_2)_y$—NH— (wherein y=1, 2, 3, or 5).

In regard to the moiety —CO—$(CH_2)_y$—NH— which may have a substituent as mentioned above for $X_1$, in a case in which y is 1, the moiety has the same meaning as an amino acid skeleton. Therefore, an amino acid derivative may also be used as $X_1$.

In a case in which $X_1$ is an amino acid derivative, the amino group at the N-terminal of the amino acid forms an amide bond with the side-chain carboxy group, and the carboxy group at the C-terminal forms an amide bond, an ester bond, or a thioester bond with an amino group, a hydroxy group, or a thiol group of $R_3$, $R_4$ or $R_5$.

The amino acid used as $X_1$ may be a naturally occurring amino acid or a non-natural amino acid, and any of the L-form and the D-form may be used without any particular limitations. For example, hydrocarbon-based amino acids such as glycine, β-alanine, alanine, leucine, and phenylalanine; acidic amino acids such as aspartic acid and glutamic acid; and basic amino acids such as lysine, arginine, and histidine may be used.

The amino acid derivative as $X_1$ is preferably an aspartic acid derivative. The aspartic acid derivative is an aspartic acid derivative in which the α-carboxy group is bonded to $R_3$, $R_4$ or $R_5$, and the β-carboxy group is in an amide form. Alternatively, the aspartic acid derivative may also be an aspartic acid derivative in which the β-carboxy group is bonded to $R_3$, $R_4$, or $R_5$, and the α-carboxy group is in an amide form. In a case in which the other carboxy group that is not involved in the bond with $R_3$, $R_4$ or $R_5$ is in an amide form, the amide form may be a (C1-C20) alkyl amide which may have a substituent, a (C5-C20) aromatic amide which may have a substituent, a (C7-C20) aralkyl amide which may have a substituent, or an amino acid residue having a protected carboxy group.

Examples of the (C1-C20) alkyl amide which may have a substituent for the aspartic acid derivative include methyl amide, ethyl amide, isopropyl amide, t-butyl amide, cyclohexyl amide, dodecyl amide, and octadecyl amide.

Examples of the (C5-C20) aromatic amide which may have a substituent for the aspartic acid derivative include phenyl amide, 4-methoxyphenyl amide, 4-dimethylaminophenyl amide, and 4-hydroxyphenyl amide. Examples of the (C7-C20) aralkyl amide which may have a substituent of the aspartic acid derivative include benzyl amide, 2-phenylethyl amide, 4-phenylbutyl amide, and 8-phenyloctyl amide. Examples of the amino acid residue having a protected carboxy group of the aspartic acid derivative include a glycinyl methyl ester group, a glycinyl ethyl ester group, a glycinyl propyl ester group, and a glycinyl benzyl ester group represented by the following Formulae (7-1) to (7-4), respectively; an alaninyl methyl ester group, an alaninyl ethyl ester group, an alaninyl propyl ester group, and an alaninyl benzyl ester group represented by the following Formulae (8-1) to (8-4), respectively; a valinyl methyl ester group, a valinyl ethyl ester group, a valinyl propyl ester group, and a valinyl benzyl ester group represented by the following Formulae (9-1) to (9-4), respectively; a leucinyl methyl ester group, a leucinyl ethyl ester group, a leucinyl propyl ester group, and a leucinyl benzyl ester group represented by the following Formulae (10-1) to (10-4), respectively; and a phenylalaninyl methyl ester group, a phenylalaninyl ethyl ester group, a phenylalaninyl propyl ester group, and a phenylalaninyl benzyl ester group represented by the following Formulae (11-1) to (11-4), respectively.

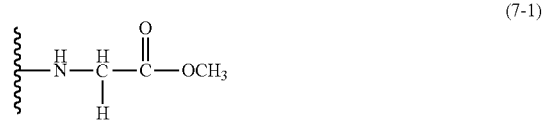

(7-1)

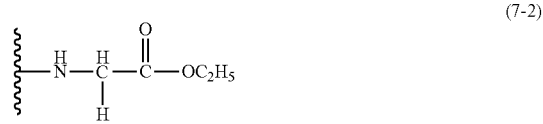

(7-2)

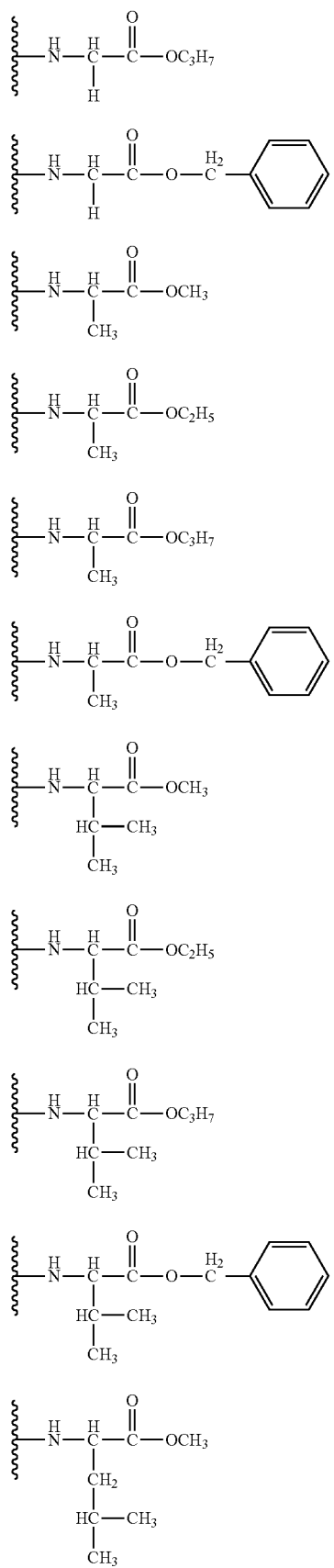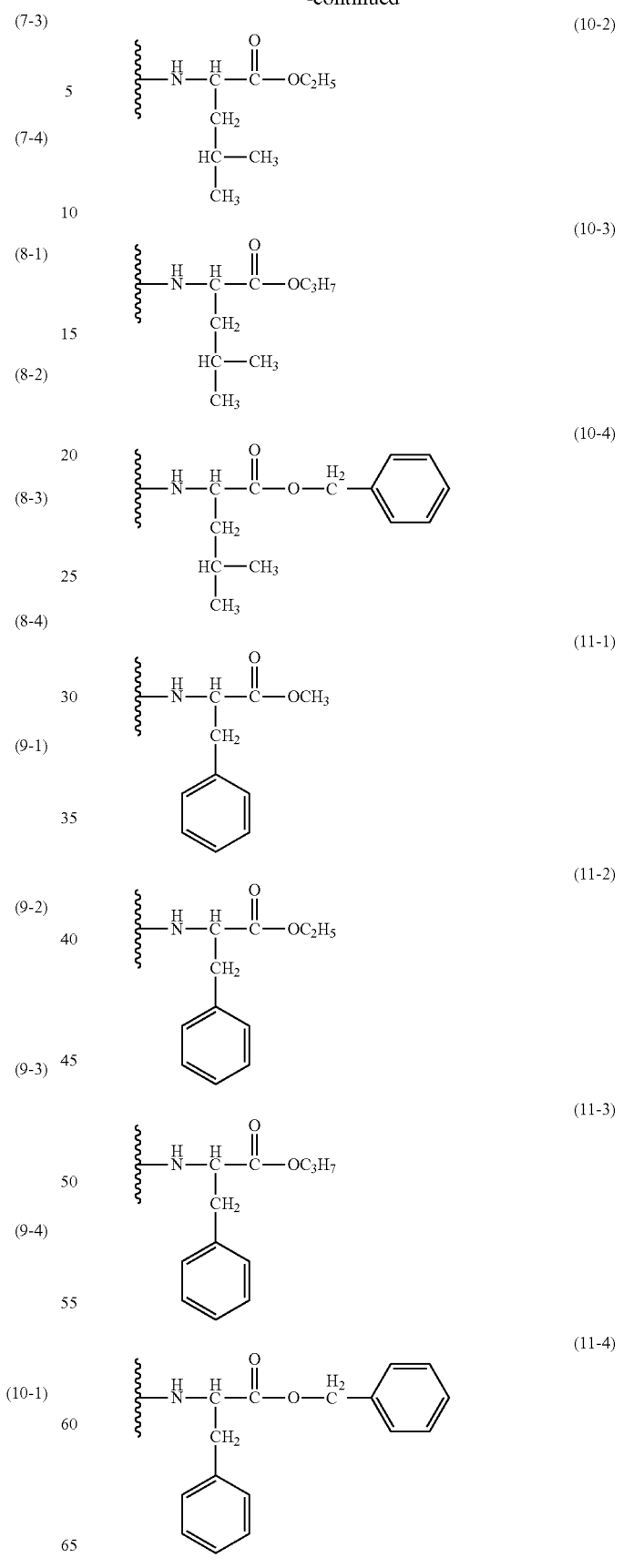

$X_1$ may also adopt an aspartic acid derivative or maleic acid derivative represented by the following General Formula (3) or General Formula (4).

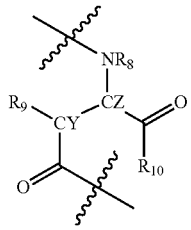 (3)

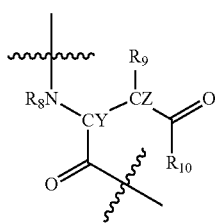 (4)

Here, in General Formula (3) and General Formula (4), $R_8$ and $R_9$ each independently represent one or more groups selected from a group consisting of a hydrogen atom or a (C1-C8) alkyl group. $R_{10}$ represents an amino group, a linear, branched or cyclic (C1-C20) alkylamino group which may have a substituent, a linear, branched or cyclic (C7-C20) aralkylamino group which may have a substituent, a (C5-C20) aromatic amino group which may have a substituent, and an amino acid residue having a protected carboxy group. CX—CY represents CH—CH or C=C (double bond) of Z-configuration.

The (C1-C8) alkyl group for $R_8$ and $R_9$ is a linear, branched or cyclic (C1-C8) alkyl group.

Examples of the linear alkyl group include a methyl group, an ethyl group, a n-propyl group, a n-butyl group, and a n-hexyl group.

Examples of the branched alkyl group include an isopropyl group, a t-butyl group, a 1-methylpropyl group, a 2-methylpropyl group, and a 2,2-dimethylpropyl group.

Examples of the cyclic alkyl group include a cyclopropyl group, a cyclobutyl group, a cyclopentyl group, and a cyclohexyl group.

In regard to $R_{10}$, examples of the linear, branched or cyclic (C1-C20) alkylamino group which may have a substituent include a methylamino group, an ethylamino group, an isopropylamino group, a t-butylamino group, a cyclohexylamino group, a n-octylamino group, a dodecylamino group, and an octadecylamino group.

Examples of the linear, branched or cyclic (C7-C20) aralkylamino group which may have a substituent include a benzylamino group, a 2-phenylethylamino group, a 4-phenylbutylamino group, and an 8-phenyloctylamino group.

Examples of the (C5-C20) aromatic amino group which may have a substituent include an anilino group, a 4-methoxyanilino group, a 4-dimethylaminoanilino group, and a 4-hydroxyanilino group.

Furthermore, $R_{10}$ may also be an amino acid residue having a protected carboxy group. Examples of the amino acid residue having a protected carboxy group include a glycinyl methyl ester group, a glycinyl ethyl ester group, a glycinyl propyl ester group, and a glycinyl benzyl ester group represented by the following Formulae (7-1) to (7-4), respectively; an alaninyl methyl ester group, an alaninyl ethyl ester group, an alaninyl propyl ester group, and an alaninyl benzyl ester group represented by the following Formulae (8-1) to (8-4), respectively; a valinyl methyl ester group, a valinyl ethyl ester group, a valinyl propyl ester group, and a valinyl benzyl ester group represented by the following Formulae (9-1) to (9-4), respectively; a leucinyl methyl ester group, a leucinyl ethyl ester group, a leucinyl propyl ester group, and a leucinyl benzyl ester group represented by the following Formulae (10-1) to (10-4), respectively; and a phenylalaninyl methyl ester group, a phenylalaninyl ethyl ester group, a phenylalaninyl propyl ester group, and a phenylalaninyl benzyl ester group represented by the following Formulae (11-1) to (11-4), respectively.

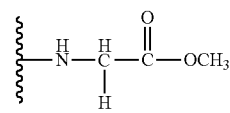 (7-1)

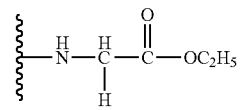 (7-2)

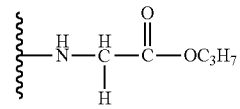 (7-3)

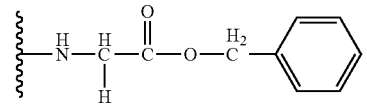 (7-4)

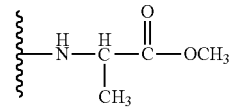 (8-1)

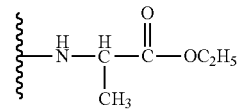 (8-2)

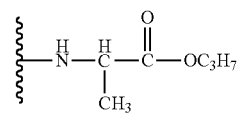 (8-3)

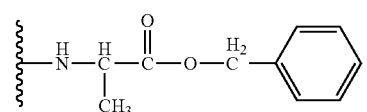 (8-4)

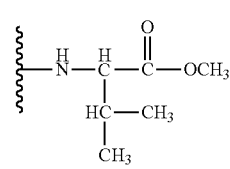 (9-1)

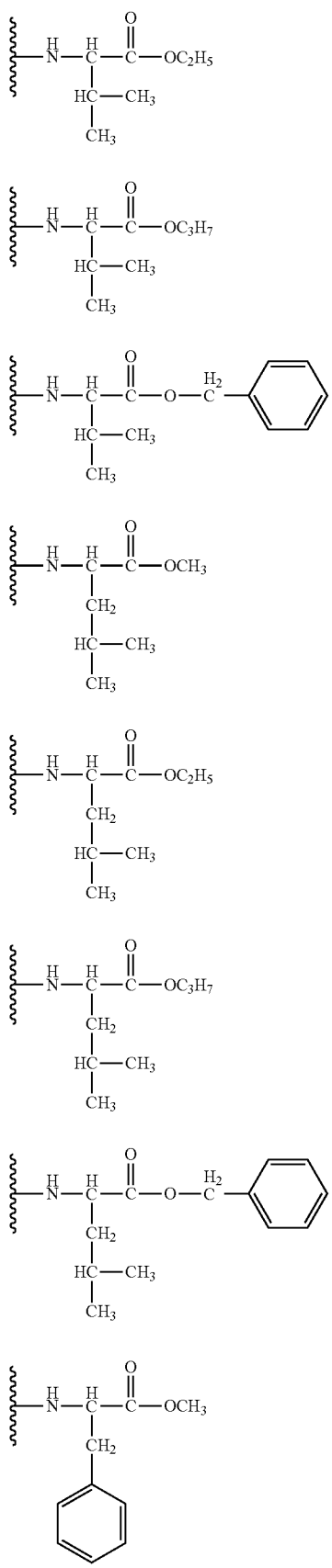

(9-2)
(9-3)
(9-4)
(10-1)
(10-2)
(10-3)
(10-4)
(11-1)

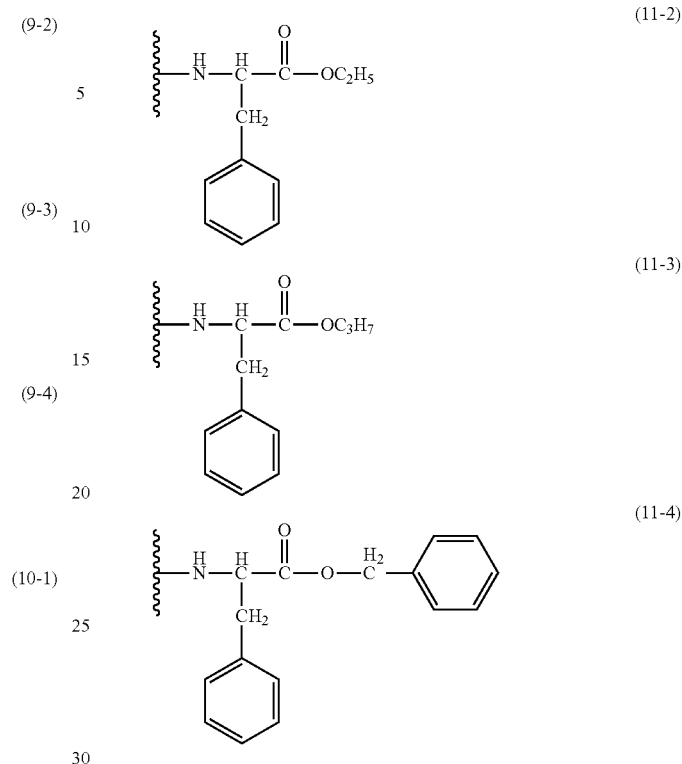

(11-2)
(11-3)
(11-4)

The average value of the total number of α-aspartic acid moieties in the polymeric derivative of tacrolimus represented by General Formula (1) is represented by a+b+c+d+e, and the number is about 2 to 300, preferably about 4 to 250, and particularly preferably about 8 to 200.

The proportion of the number of aspartic acid units (a) bonded to tacrolimus with respect to the total number of α-aspartic acid units (a+b+c+d+e) is 1% to 99%, preferably 1% to 80%, and more preferably 1 to 60%. Since the aspartic acid moieties need to co-exist with the polyethylene glycol segment-bonded aspartic acid units, when the balance is taken into consideration, the proportion is preferably 1% to 50%, more preferably 1% to 30%, and particularly preferably 5% to 30%.

Furthermore, the number of α-aspartic acid units (a) is 1 to 200, preferably about 2 to 150, and particularly preferably about 2 to 100, or about 2 to 40.

The proportion of the number of aspartic acid units (b) bonded to the polyethylene glycol segment with respect to the total number of α-aspartic acid units (a+b+c+d+e) is 1% to 99%, preferably 1% to 80%, and more preferably 1% to 60%. Since the polyethylene glycol segment-bonded aspartic acid units need to co-exist with the tacrolimus-bonded aspartic acid units described above, when the balance is taken into consideration, the proportion is preferably 1% to 40%, and particularly preferably 2% to 40%.

Furthermore, the number of α-aspartic acid units (b) is 1 to 200, preferably about 1 to 150, and particularly preferably about 1 to 100, or about 2 to 40.

The average value of the total number of aspartic acid units in the polymeric derivative of tacrolimus represented by General Formula (2) is represented by f+g+h+i+j+k+l+m+n, and the average value is about 2 to 300, preferably about 4 to 250, and particularly preferably 8 to 200.

The proportion of the number of aspartic acid units bonded to tacrolimus (f+g) with respect to the total number of aspartic acid units (f+g+h+i+j+k+l+m+n) is 1% to 99%, preferably 1% to 80%, and more preferably 1% to 60%. Since the aspartic acid units bonded to tacrolimus need to co-exist with the polyethylene glycol segment-bonded aspartic acid units, when the balance is taken into consideration, the proportion is preferably 1% to 50%, more preferably 1% to 30%, and particularly preferably 5% to 30%.

Furthermore, the number of aspartic acid units bonded to tacrolimus (f+g) is 1 to 200, preferably about 2 to 150, and particularly preferably about 2 to 100, or about 2 to 40.

The proportion of the number of aspartic acid units bonded to polyethylene glycol segment (h+i) with respect to the total number of aspartic acid units (f+g+h+i+j+k+l+m+n) is 1% to 99%, preferably 1% to 80%, and more preferably 1% to 60%. Since the aspartic acid units bonded to the polyethylene glycol segment need to co-exist with the tacrolimus-bonded aspartic acid units described above, when the balance is taken into consideration, the proportion is preferably 1% to 40%, and particularly preferably 2% to 40%.

Furthermore, the number of aspartic acid units bonded to tacrolimus (h+i) is 1 to 200, preferably about 1 to 150, and particularly preferably about 1 to 100, or about 2 to 40.

The proportion of α-aspartic acid units (f+h+j+l) with respect to the total number of aspartic acid units (f+g+h+i+j+k+l+m+n) is 1% to 80%, and preferably 1% to 50%. This proportion may be appropriately changed by, for example, selecting the deprotection conditions for the protective groups of the polyaspartic acid, or the like.

Regarding the molecular weight of the polymeric derivative of tacrolimus of the present invention, a calculated value obtained by summing the various constituent molecular weights of the constituent moieties described above is employed as the "molecular weight of the polymeric derivative of tacrolimus". That is, a calculated value obtained by summing (1) the molecular weight of the polyaspartic acid main chain, (2) the total molecular weight of polyethylene glycol segments obtained by multiplying the molecular weight of the polyethylene glycol segment by the bonding number, (3) the total molecular weight of tacrolimus obtained by multiplying the molecular weight of the residue of tacrolimus by the bonding number, (4) the total molecular weight of $X_1$ residues obtained by multiplying the molecular weight of any $X_1$ residue bonded to polyethylene glycol segment by the bonding number, and (5) the total molecular weight of $X_1$ residues obtained by multiplying the molecular weight of any $X_1$ residue bonded to tacrolimus by the bonding number, is designated as the molecular weight.

Regarding the molecular weight of the polyaspartic acid derivative, molecular weight specification on the basis of accuracy in the order of the kilodalton unit is required. Therefore, the method for analyzing the various constituent moieties is not particularly limited as long as the method is an analysis method with an accuracy sufficient for the molecular weight measurement of the polyaspartic acid derivative in the order of the kilodalton unit, and various analysis methods may be selected as appropriate. In the following description, a preferred analysis method for the various constituent moieties will be described.

The (1) molecular weight of the polyaspartic acid main chain is a calculated value obtained by multiplying the molecular weight of the polymerized monomer unit of the main chain by the degree of polymerization. Regarding the degree of polymerization, a degree of polymerization calculated from the integral value of $^1$H-NMR, a degree of polymerization calculated by an amino acid analysis, or a degree of polymerization calculated by neutralization titration may be used.

The (2) total molecular weight of the polyethylene glycol segments is a calculated value obtained by multiplying the molecular weight of the polyethylene glycol segment by the bonding number. Regarding the molecular weight of the polyethylene glycol segment, the average molecular weight of the polyethylene glycol segment-structured compound used, which is determined based on the peak top molecular weight measured by a GPC method relative to the standard products of polyethylene glycol, is employed.

Regarding the bonding number of the polyethylene glycol segment, a method of determining the bonding number by cleaving the polyethylene glycol segments from the polymeric derivative of tacrolimus and quantitatively analyzing the free polyethylene glycol segments may be used. Alternatively, a method of calculating the bonding number from the consumption rate of the polyethylene glycol segments in a reaction for introducing polyethylene glycol segments into the polyaspartic acid main chain may also be used.

The (3) total molecular weight of tacrolimus is a calculated value obtained by multiplying the molecular weight of the residue of tacrolimus by the bonding number. Regarding the bonding number of tacrolimus, a method of determining the bonding number by hydrolyzing the polymeric derivative of tacrolimus, derivatizing tacrolimus in a free form or a decomposition product thereof as necessary, and quantitatively analyzing tacrolimus or the derivative by high performance liquid chromatography (HPLC) may be used. Alternatively, a method of calculating the bonding number from the consumption rate of tacrolimus in a reaction for introducing tacrolimus into the polyaspartic acid main chain may also be used.

The (4) total molecular weight of any $X_1$ residues bonded to the polyethylene glycol segments is a calculated value obtained by multiplying the molecular weight of the $X_1$ residue by the bonding number. A method of calculating the total molecular weight from the consumption rate of $X_1$ in a reaction for introducing $X_1$ into the polyaspartic acid main chain may also be used.

The (5) total molecular weight of any $X_1$ residues bonded to tacrolimus is a calculated value obtained by multiplying the molecular weight of the $X_1$ residue by the bonding number. A method of calculating the total molecular weight from the consumption rate of $X_1$ in a reaction for introducing $X_1$ into the polyaspartic acid main chain may also be used.

The polymeric derivative of tacrolimus of the present invention has a feature that the mass percentage content of the polyethylene glycol segment in the polymeric derivative is from 30% by mass to 95% by mass. The mass percentage content of the polyethylene glycol segment may be calculated based on the content ratio of the (2) total molecular weight of the polyethylene glycol segments with respect to the molecular weight of the polymeric derivative of tacrolimus. That is, the mass percentage content of the polyethylene glycol segment is calculated by the following formula.

(Calculation Formula)

Mass percentage content of PEG (%)=Total molecular weight of PEG/molecular weight of polymeric derivative of TAC×100

Remark) PEG: Polyethylene glycol segment
Remark) TAC: Tacrolimus

A more preferred range of the mass percentage content of the polyethylene glycol segment is from 30% by mass to 95% by mass, and particularly preferably from 40% by mass to 95% by mass.

In regard to the polymeric derivative of tacrolimus of the present invention, the mass percentage content of tacrolimus in the polymeric derivative is preferably from 2% by mass to 50% by mass.

The mass percentage content of the macrolide immunosuppressant in the polyamino acid derivative may be calculated based on the content ratio of the (3) total molecular weight of tacrolimus with respect to the molecular weight of the polyaspartic acid derivative described above. That is, the mass percentage content of tacrolimus is calculated by the following formula.

(Calculation Formula)

Mass percentage content of TAC (%)=Total molecular weight of TAC/molecular weight of polymeric derivative of TAC×100

Remark) TAC: Tacrolimus

A more preferred range of the mass percentage content of tacrolimus is from 2% by mass to 50% by mass. It is particularly preferable that the tacrolimus content is from 2% by mass to 40% by mass.

The polymeric derivative of tacrolimus of the present invention is obtained by bonding side-chain carboxy groups of a polyaspartic acid derivative to an alcoholic hydroxy group of tacrolimus and a polyethylene glycol segment via an ester bond, an amide bond, and/or a thioester group using a dehydration condensing agent in an organic solvent, and the present production method is also included in the present invention. That is, the method is a production method of subjecting a block copolymer of a polyethylene glycol structural moiety-polyaspartic acid, and tacrolimus in which functional groups other than the group to be reacted have been protected as necessary, to a reaction of using a dehydration condensing agent such as dicyclohexylcarbodiimide (DCC), diisopropylcarbodiimide (DIPCI), 1-ethyl-3-(3-dimethylaminopropyl)carbodiimide hydrochloride (EDCI), or 1-ethoxycarbonyl-2-ethoxy-1,2-dihydroxyquinolinone (EEDQ), in an organic solvent that dissolves both the compounds, preferably in an aprotic polar solvent such as N,N-dimethylformamide (DMF), 1,3-dimethyl-2-imidazolidinone (DMI), or N-methylpyrrolidone (NMP), at 0° C. to 180° C., and preferably 5° C. to 50° C. Furthermore, a reaction aid such as N,N-dimethylaminopyridine (DMAP) may also be used at the time of the condensation reaction. After the condensation reaction, deprotection is performed as necessary, and after operations of conventional separation and purification, a polymeric derivative of tacrolimus is produced.

Furthermore, a polymeric derivative of tacrolimus, in which $R_5$ is a —N($R_6$)CONH($R_7$) group, may also be obtained by using the above-mentioned carbodiimides as condensing agents.

Regarding a method for introducing side-chain carboxy groups of a polyaspartic acid derivative, tacrolimus, and a polyethylene glycol segment, a method of activating the side-chain carboxy groups of a polyaspartic acid derivative by the above-described method, and then reacting, under basic conditions, the activated side-chain carboxy groups with alcoholic hydroxy groups of corresponding tacrolimus and a corresponding polyethylene glycol segment in amounts that are wished to be added; a method of activating corresponding tacrolimus and a corresponding polyethylene glycol segment, and then reacting the activation products with side-chain carboxy groups of a polyaspartic acid derivative; and the like may also be employed.

Regarding the order of introduction of tacrolimus and the polyethylene glycol segment into the side-chain carboxy groups of the polyamino acid derivative, it is acceptable that tacrolimus is introduced, and then the polyethylene glycol segment is introduced; it is also acceptable that the polyethylene glycol segment is introduced, and then tacrolimus is introduced; or both may be introduced simultaneously. Furthermore, after a polymeric derivative having tacrolimus or a polyethylene glycol segment introduced thereinto is synthesized and purified, unreacted carboxy groups in the polyamino acid derivative may be reactivated by the same reaction, and tacrolimus or the polyethylene glycol segment may also be introduced into these reactivated carboxy groups. However, the production method for the polymeric derivative of tacrolimus of the present invention is not limited to the methods described above.

The polymeric derivative of tacrolimus of the present invention has a property of slowly releasing tacrolimus after being administered into the living body, and is offered for use as a medicine containing this tacrolimus as an active ingredient.

The use of the polymeric derivative of tacrolimus of the present invention as a pharmaceutical product is not particularly limited as long as the polymeric derivative is used for a disease for which tacrolimus provides a therapeutic effect. For example, the polymeric derivative of tacrolimus is appropriate for a medicine used for the treatment of autoimmune diseases, inflammatory diseases, allergic diseases, and suppression of rejection in organ transplantation and bone marrow transplantation. Particularly preferably, the polymeric derivative of tacrolimus is a medicine for the treatment of autoimmune diseases or inflammatory diseases. Examples of the autoimmune diseases include rheumatoid arthritis, systemic erythematodes, and ulcerative colitis, and examples of the inflammatory diseases include interstitial pneumonitis.

A medicine containing a polymeric derivative of tacrolimus of the present invention may include other additives that are conventionally accepted as pharmaceutical products. Examples of the additives include an excipient, an extending agent, a filler, a binder, a wetting agent, a disintegrant, a lubricating agent, a surfactant, a dispersant, a buffering agent, a preservative, a dissolution aid, an antiseptic agent, a flavoring agent, a soothing agent, a stabilizer, and a tonicity adjusting agent.

A medicine containing the polymeric derivative of tacrolimus of the present invention may be prepared as a pharmaceutical preparation for treatment. The preparation may be administered by any administration method such as peroral, injection, intrarectal administration, portal injection, mixing into the perfusate of an organ, or topical administration into a diseased organ; however, preferably parenteral administration is preferred, and intravenous administration by injection, intraarterial administration, or topical administration into a diseased organ is more preferred. Usually, for example, water, physiological saline, a 5% glucose or mannitol solution, a water-soluble organic solvent (for example, glycerol, ethanol, dimethyl sulfoxide, N-methylpyrrolidone, polyethylene glycol, Cremophor, or a mixed liquid thereof), and a mixed liquid of water and the water-soluble organic solvent are used.

The amount of administration of the polymeric derivative of tacrolimus of the present invention may be definitely variable depending on the gender, age, physiological conditions, diseased state, and the like of the patient; however, the polymeric derivative of tacrolimus is usually administered parenterally in an amount of 0.01 to 500 mg/m$^2$, and preferably 0.1 to 250 mg/m$^2$, per day for an adult. Administration by injection is carried out through a vein, an artery, a diseased area (inflammation area), and the like.

The polymeric derivative of tacrolimus of the present invention accumulates in a diseased area, and exhibits a superior effect with a low amount of administration, compared to simple tacrolimus drug. Furthermore, since enzyme-independent release of a physiologically active substance and maintenance of the concentration in blood are enabled, the control of the amount of administration depending on the blood kinetics (blood trough concentration) becomes unnecessary, and a long interval of administration and safety are markedly enhanced. Therefore, the polymeric derivative of tacrolimus of the present invention is an immunosuppressant or an anti-inflammatory agent useful for the treatment and prevention of rejection to a transplant of an organ or a tissue, a graft-versus-host reaction, an autoimmune disease, an infectious disease, and the like.

EXAMPLES

Hereinafter, the present invention will be further explained by Examples. However, the present invention is not intended to be limited to these Examples. Also, the compounds of the present invention were used after being formulated as necessary.

Synthesis Example 1

Synthesis of Polyethylene Glycol-αρ-Polyaspartic Acid Block Copolymer (Polyethylene Glycol Molecular Weight: 12,000, Degree of Polymerization of Polyaspartic Acid: 95) (Compound 1)

A polyethylene glycol having a methoxy group at one end and a 3-aminopropyl group at another end (SUNBRIGHT MEPA-12T, manufactured by NOF Corp., average molecular weight 12 kilodaltons, 10.0 g) was dissolved in dimethyl sulfoxide (DMSO, 130 mL), subsequently γ-benzyl-L-aspartic acid-N-carboxylic acid anhydride (BLA-NCA, 13.8 g, 200 equivalents) was added to the solution, and the mixture was stirred overnight at 32.0° C. The reaction liquid was added dropwise for one hour to a mixed solvent of ethanol (755 mL) and diisopropyl ether (3,101 L), and the mixture was stirred for one hour at room temperature. A precipitate was collected by filtration and then dried in a vacuum, and thus a solid (41.8 g) was obtained.

The solid (40.0 g) thus obtained was dissolved in N,N-dimethylformamide (DMF, 800 mL), and acetic anhydride (1.26 mL) was added to the solution. The mixture was stirred at 32.5° C. The reaction liquid was added dropwise to a mixed solvent of ethanol (800 mL) and diisopropyl ether (7,200 mL), and the mixture was stirred at room temperature. A precipitate was collected by filtration and then dried in a vacuum, and a solid (32.2 g) was obtained. The solid (30 g) thus obtained was suspended in acetonitrile (MeCN, 1,200 mL), subsequently a 0.2 N aqueous solution of sodium hydroxide (1,200 mL) and purified water (180 mL) were added to the suspension, and the mixture was subjected to hydrolysis at 23° C. The reaction liquid was neutralized by adding 2 N hydrochloric acid thereto, and then acetonitrile was removed by concentration under reduced pressure. The concentrate was washed three times using ethyl acetate (1,800 mL). The aqueous layer was concentrated under reduced pressure, and the pH of the solution was adjusted to 10.7 using a 1 N aqueous solution of sodium hydroxide. Sodium chloride (60.8 g) was added to the solution, and then the solution was purified and desalinated using partition/adsorption resin column chromatography and ion exchange resin column chromatography. A solution thus eluted was concentrated under reduced pressure and then freeze-dried, and Compound 1 (15.1 g) was obtained. The degree of polymerization of aspartic acid in one molecule of the present compound based on the titration value obtained using a 0.1 N potassium hydroxide solution was 94.9.

Synthesis Example 2

Synthesis of Polyethylene Glycol-αβ-Polyaspartic Acid Block Copolymer (Polyethylene Glycol Molecular Weight: 12,000, Degree of Polymerization of Polyaspartic Acid: 43) (Compound 2)

The indicated Compound 2 was obtained by using 52.2 equivalents of BLA-NCA for a polyethylene glycol having a methoxy group at one end and a 3-aminopropyl group at another end, according to the method described in Synthesis Example 1. The degree of polymerization of aspartic acid in one molecule of the present compound based on the titration value obtained using a 0.1 N potassium hydroxide solution was 43.2.

Synthesis Example 3

Synthesis of Polyethylene Glycol-αβ-Polyaspartic Acid Block Copolymer (Polyethylene Glycol Molecular Weight: 12,000, Degree of Polymerization of Polyaspartic Acid: 73) (Compound 3)

A polyethylene glycol having a methoxy group at one end and a 3-aminopropyl group at another end (SUNBRIGHT MEPA-12T, manufactured by NOF Corp., average molecular weight 12 kilodaltons, 10.0 g) was dissolved in DMSO (190 mL), subsequently BLA-NCA (8.89 g, 129 equivalents) was added to the solution, and the mixture was stirred overnight at 32° C. The reaction liquid was added dropwise for one hour to a mixed solvent of ethanol (400 mL) and diisopropyl ether (1,600 mL), and the mixture was stirred for one hour at room temperature. A precipitate was collected by filtration and then dried in a vacuum, and a solid (26.5 g) was obtained.

The solid (23.0 g) thus obtained was dissolved in acetonitrile (460 mL), and acetic anhydride (724 mL) was added to the solution. The mixture was stirred for 3 hours at 35° C. and then was cooled to 23° C. A 0.2 N sodium hydroxide solution (539 mL) was added dropwise to the reaction liquid, and the mixture was subjected to hydrolysis at 23° C. The reaction liquid was neutralized by adding 2 N hydrochloric acid thereto, and then acetonitrile was removed by concentration under reduced pressure. Subsequently, the concentrate was washed three times using ethyl acetate (720 mL). The aqueous layer was concentrated under reduced pressure, and then the pH of the solution was adjusted to 10.6 by using a 1 N sodium hydroxide solution. Sodium chloride (57.5 g) was added thereto, and then the solution was purified using partition/adsorption resin column chromatography and subsequent ion exchange resin column chromatography. A solution thus eluted was concentrated under reduced pressure and then freeze-dried, and Compound 3 (13.0 g) was obtained. The degree of polymerization of aspartic acid in one molecule of the present compound based on the titration value obtained using a 0.1 N potassium hydroxide solution was 72.8.

Synthesis Example 4

Synthesis of αβ-Polyaspartic Acid Polymer (Degree of Polymerization of Polyaspartic Acid: 78) (Compound 4)

n-Butylamine (manufactured by Tokyo Chemical Industry Co., Ltd., 18.3 mg) was dissolved in DMSO (30 mL), subsequently BLA-NCA (5.61 g, 90 equivalents) was added to the solution, and the mixture was stirred overnight at 30° C. The reaction liquid was added dropwise to a mixed solvent of ethanol (120 mL) and diisopropyl ether (480 mL), and the mixture was stirred at room temperature. A precipitate was collected by filtration and then dried in a vacuum, and a solid was obtained. 1,3-Dimethyl-2-imidazolidinone (DMI, 35 mL) was added to the total amount of the solid thus obtained, the solid was dissolved therein at 78° C., and then 2.5 mL of acetic anhydride was added thereto at 70° C. After the mixture was stirred for 3 hours, the reaction liquid was added dropwise to a mixed solution of ethyl acetate (175 mL) and diisopropyl ether (700 mL), and the mixture was stirred overnight at room temperature. A precipitate was collected by filtration and then dried in a vacuum, and a solid (3.74 g) was obtained.

The solid (3.74 g) thus obtained was dissolved in acetonitrile (30 mL), a 0.2 N sodium hydroxide solution (138 mL) was added to the solution, and the mixture was subjected to hydrolysis at room temperature. After the reaction, acetonitrile was removed by concentration under reduced pressure, and then the concentrate was washed three times using ethyl acetate (420 mL). The aqueous layer was concentrated under reduced pressure, subsequently purified using ion exchange resin column chromatography, and subjected to freeze-drying. Thus, Compound 4 (2.29 g) was obtained. The degree of polymerization of aspartic acid in one molecule of the present compound based on NMR was 78.

Synthesis Example 5

Synthesis of αβ-Polyaspartic Acid Polymer (Degree of Polymerization of Polyaspartic Acid: 112) (Compound 5)

n-Butylamine (manufactured by Tokyo Chemical Industry Co., Ltd., 15.8 mg) was dissolved in DMSO (30 mL), subsequently BLA-NCA (7.26 g, 135 equivalents) was added to the solution, and the mixture was stirred overnight at 30° C. The reaction liquid was added dropwise to a mixed solvent of ethanol (120 mL) and diisopropyl ether (480 mL), and the mixture was stirred at room temperature. A precipitate was collected by filtration and then dried in a vacuum, and a solid (5.37 g) was obtained. DMI (35 mL) was added to the solid (5.37 g) thus obtained, the solid was dissolved therein at 80° C., and then 2.5 mL of acetic anhydride was added thereto at 68° C. After the mixture was stirred for 3 hours, the reaction liquid was added dropwise to a mixed solution of ethyl acetate (200 mL) and diisopropyl ether (800 mL), and the mixture was stirred overnight at room temperature. A precipitate was collected by filtration and then dried in a vacuum, and a solid (5.16 g) was obtained.

The solid (5.16 g) thus obtained was dissolved in acetonitrile (22 mL), a 0.2 N sodium hydroxide solution (167 mL) was added thereto, and the mixture was subjected to hydrolysis at room temperature. After the reaction, acetonitrile was removed by concentration under reduced pressure, and then the concentrate was washed three times using ethyl acetate (510 mL). The aqueous layer was concentrated under reduced pressure, and then the concentrate was purified using ion exchange resin column chromatography and was subjected to freeze-drying. Thus, Compound 5 (3.00 g) was obtained. The degree of polymerization of aspartic acid in one molecule of the present compound based on NMR was 112.

Synthesis Example 6

Synthesis of Polyethylene Glycol-α-Polyaspartic Acid Block Copolymer (Polyethylene Glycol Molecular Weight: 12,000, Degree of Polymerization of Polyaspartic Acid: 87) (Compound 6)

A polyethylene glycol having a methoxy group at one end and a 3-aminopropyl group at another end (SUNBRIGHT MEPA-12T, manufactured by NOF Corp., average molecular weight 12 kilodaltons, 6.0 g) was dissolved in DMSO (114 mL), subsequently BLA-NCA (15.0 g, 120 equivalents) was added to the solution, and the mixture was stirred overnight at 30° C. The reaction liquid was added dropwise to a mixed solvent of ethanol (228 mL) and diisopropyl ether (912 mL), and the mixture was stirred at room temperature. A precipitate was collected by filtration and then dried in a vacuum, and a solid (23.8 g) was obtained. The total amount of the solid thus obtained was dissolved in DMF (200 mL), and acetic anhydride (0.75 mL) was added to the solution. The mixture was stirred for 3 hours at 30° C. The reaction liquid was added dropwise to a mixed solvent of ethyl acetate (200 mL) and diisopropyl ether (1,800 mL), and the mixture was stirred at room temperature. A precipitate was collected by filtration and then dried in a vacuum, and a solid (15.8 g) was obtained.

The solid (8.72 g) thus obtained was dissolved in 1-methyl-2-pyrrolidone (NMP, 140 mL), subsequently 10% palladium-carbon (0.87 g) was added to the solution, and the mixture was subjected to hydrogenolysis overnight at 35° C. Activated carbon was added to the reaction liquid, the mixture was stirred for one hour, and then the 10% palladium-carbon was separated by filtration. The filtrate was added dropwise to a mixed solvent of ethyl acetate (200 mL) and diisopropyl ether (1,000 mL) and the mixture was stirred overnight at room temperature. A precipitate was collected by filtration and then dried in a vacuum, and a solid (4.18 g) was obtained. The total amount of the solid was dissolved in purified water (418 mL), and sodium chloride (20.9 g) was added to dissolve therein. The pH of the solution was adjusted to 11.0 with a 2 N sodium hydroxide solution, and then the solution was purified using partition/adsorption resin column chromatography and subsequent ion exchange resin column chromatography. A solution thus eluted was concentrated under reduced pressure and then freeze-dried. Thus, Compound 6 (760 mg) was obtained. The degree of polymerization of aspartic acid in one molecule of the present compound based on NMR was 87.

Synthesis Example 7

Synthesis of Polyethylene Glycol-α-Polyaspartic Acid Block Copolymer (Polyethylene Glycol Molecular Weight: 12,000, Degree of Polymerization of Polyaspartic Acid: 40) (Compound 7)

The indicated Compound 7 was obtained by using 51.3 equivalents of BLA-NCA for a polyethylene glycol having a methoxy group at one end and a 3-aminopropyl group at another end according to the method described in Synthesis Example 6. At this time, DMF was used instead of NMP. The degree of polymerization of aspartic acid in one molecule of the compound based on the titration value obtained using a 0.1 N potassium hydroxide solution was 40.2.

Synthesis Example 8

Synthesis of Polyethylene Glycol-α-Polyaspartic Acid Block Copolymer (Polyethylene Glycol Molecular Weight: 12,000, Degree of Polymerization of Polyaspartic Acid: 90) (Compound 8)

A polyethylene glycol having a methoxy group at one end and a 3-aminopropyl group at another end (SUNBRIGHT MEPA-12T, manufactured by NOF Corp., average molecular weight 12 kilodaltons, 10.0 g) was dissolved in DMSO (200 mL), subsequently BLA-NCA (28.7 g, 140 equivalents) was added to the solution, and the mixture was stirred overnight at 32.5° C. The reaction liquid was added dropwise to a mixed solvent of ethanol (400 mL) and diisopropyl ether (1,600 mL), and the mixture was stirred at room temperature. A precipitate was collected by filtration and then dried in a vacuum, and a solid (28.6 g) was obtained. The solid (18.1 g) thus obtained was dissolved in NMP (181 mL), and acetic anhydride (0.57 mL) was added to the solution. The mixture was stirred overnight at 30° C. The reaction liquid was added dropwise to a mixed solvent of diisopropyl ether (2,000 mL), and the mixture was stirred at room temperature. A precipitate was collected by filtration and then dried in a vacuum, and a solid was obtained.

The solid (15.3 g) thus obtained was dissolved in NMP (155 mL), subsequently 10% palladium-carbon (3.46 g) was added to the solution, and the mixture was subjected to hydrogenolysis overnight at 35° C. Activated carbon was added to the reaction liquid, the mixture was stirred for 30 minutes, and then 10% palladium-carbon was separated by filtration. The filtrate was added dropwise to a mixed solvent of diisopropyl ether (3,700 mL), and the mixture was stirred at room temperature. A precipitate was collected by filtration and then dried in a vacuum, and a solid (5.64 g) was obtained. The solid (4.53 g) thus obtained was dissolved in purified water (453 mL), the pH of the solution was adjusted to 11.0 with a sodium hydroxide solution, and then the solution was purified using anion exchange resin column chromatography and subsequent cation exchange resin column chromatography. A solution thus eluted was concentrated under reduced pressure and then freeze-dried. Thus, Compound 8 (3.43 g) was obtained. The degree of polymerization of aspartic acid in one molecule of the present compound based on the titration value obtained using a 0.1 N potassium hydroxide solution was 90.0.

Example 1

Polymeric derivative in which in regard to General Formula (2), $R_1$ represents a structure of General Formula (6); $R_2$ represents an acetyl group; $R_3$ represents a residue of an alcoholic hydroxy group of tacrolimus; $R_4$ represents a structure of General Formula (5); $R_5$ represents an isopropylaminocarbonylisopropylamino group; $R_{11}$ and $R_{13}$ each represent a methyl group; $R_{12}$ and $R_{14}$ each represent a trimethylene group; $X_1$ represents a bond; $X_2$ represents a —NH— group; the average values of o and p are each 272; the average value of f+g+h+i+j+k+l+m+n is 43.2; the average value of f+g is 7.0; and the average value of h+i is 5.2 (Compound 9)

Compound 2 (245 mg), tacrolimus (250 mg), and a polyethylene glycol having a methoxy group at one end and a 3-aminopropyl group at another end (SUNBRIGHT MEPA-12T, manufactured by NOF Corp., average molecular weight 12 kilodaltons, 862 mg) were dissolved in NMP (6.2 mL), and N,N-dimethylaminopyridine (DMAP, 37.9 mg) and N,N'-diisopropylcarbodiimide (DIPCI, 192 μL) were added to the solution at 25° C. The mixture was stirred overnight. The reaction liquid was added dropwise to diisopropyl ether (186 mL), and the mixture was stirred. A precipitate was collected by filtration and dried in a vacuum. A solid thus obtained was dissolved in acetonitrile (7 mL) and then purified water (7 mL) and an ion exchange resin (7 mL) were added to the solution. The mixture was stirred, and then the ion exchange resin was separated by filtration. The filtrate was concentrated under reduced pressure and then freeze-dried, and thus Compound 9 (1.12 g) was obtained. The tacrolimus content of Compound 9 was calculated to be 6.84%.

Example 2

Polymeric derivative in which in regard to General Formula (2), $R_1$ represents a structure of General Formula (6); $R_2$ represents an acetyl group; $R_3$ represents a residue of an alcoholic hydroxy group of tacrolimus; $R_4$ represents a structure of General Formula (5); $R_5$ represents an isopropylaminocarbonylisopropylamino group; $R_{11}$ and $R_{13}$ each represent a methyl group; $R_{12}$ and $R_{14}$ each represent a trimethylene group; $X_1$ represents a bond; $X_2$ represents a —NH— group; the average values of o and p are each 272; the average value of f+g+h+i+j+k+l+m+n is 72.8; the average value of f+g is 14.1; and the average value of h+i is 5.0 (Compound 10)

Compound 3 (130 mg), tacrolimus (240 mg), and a polyethylene glycol having a methoxy group at one end and a 3-aminopropyl group at another end (SUNBRIGHT MEPA-12T, manufactured by NOF Corp., average molecular weight: 12 kilodaltons, 382 mg) were dissolved in NMP (4.6 mL), and DMAP (28.3 mg) and DIPCI (143 μL) were added to the solution at 25° C. The mixture was stirred overnight. The reaction liquid was added dropwise to diisopropyl ether (139 mL), and the mixture was stirred. A precipitate was collected by filtration and dried in a vacuum, and a solid thus obtained was dissolved in acetonitrile (5 mL). Subsequently, purified water (5 mL) and an ion exchange resin (5 mL) were added to the solution, the mixture was stirred, and then the ion exchange resin was separated by filtration. The filtrate was concentrated under reduced pressure and then freeze-dried, and thus Compound 10 (528 mg) was obtained. The tacrolimus content of Compound 10 was calculated to be 12.3%.

Example 3

Polymeric derivative in which in regard to General Formula (2), $R_1$ represents a structure of General Formula (6); $R_2$ represents an acetyl group; $R_3$ represents a residue of an alcoholic hydroxy group of tacrolimus; $R_4$ represents a structure of General Formula (5); $R_5$ represent an isopropylaminocarbonylisopropylamino group; $R_{11}$ and $R_{13}$ each represent a methyl group; $R_{12}$ and $R_{14}$ each represent a trimethylene group; $X_1$ represents a bond; $X_2$ represents a —NH— group; the average values of o and p are each 272; the average value of f+g+h+i+j+k+l+m+n is 94.9; the average value of f+g is 7.4; and the average value of h+i is 12.8 (Compound 11)

Compound 1 (5.30 g), tacrolimus (12 g), and a polyethylene glycol having a methoxy group at one end and a 3-aminopropyl group at another end (SUNBRIGHT MEPA-12T, manufactured by NOF Corp., average molecular weight 12 kilodaltons, 34.7 g) were dissolved in NMP (430 mL), and DMAP (1.31 g) and DIPCI (6.59 mL) were added to the solution at 25° C. The mixture was stirred for two nights. The reaction liquid was added dropwise to diisopropyl ether (13 L), and the mixture was stirred. A precipitate was collected by filtration and dried in a vacuum, and thus a solid (41.5 g) was obtained. The solid (41.0 g) thus obtained was dissolved in DMF (575 mL), and an ion exchange resin (130 mL) was added to the solution. The mixture was stirred for one hour, and then the ion exchange resin was separated by filtration. The filtrate was added dropwise to diisopropyl ether (18.5 L), and the mixture was stirred. A precipitate was collected by filtration and dried in a vacuum, and thus a solid (39.5 g) was obtained. The solid (37.0 g) thus obtained was dissolved in acetonitrile (370 mL), subsequently purified water (370 mL) was added to the solution, and the mixture was concentrated under reduced pressure and freeze-dried. Thus, Compound 11 (37.2 g) was obtained. The tacrolimus content of Compound 11 was calculated to be 3.22%.

Example 4

Polymeric derivative in which in regard to General Formula (2), $R_1$ represents a structure of General Formula (6); $R_2$ represents an acetyl group; $R_3$ represents a residue of an alcoholic hydroxy group of tacrolimus; $R_4$ represents a structure of General Formula (5); $R_5$ represents an isopropylaminocarbonylisopropylamino group; $R_{11}$ and $R_{13}$ each represent a methyl group; $R_{12}$ and $R_{14}$ each represent a trimethylene group; $X_1$ represents a bond; $X_2$ represents a —NH— group; the average values of o and p are each 272; the average value of f+g+h+i+j+k+l+m+n is 72.8; the average value of f+g is 5.5; and the average value of h+i is 9.1 (Compound 12)

Compound 3 (4.50 g), tacrolimus (4.13 g), and a polyethylene glycol having a methoxy group at one end and a 3-aminopropyl group at another end (SUNBRIGHT MEPA-12T, manufactured by NOF Corp., average molecular weight 12 kilodaltons, 24.1 g) were dissolved in NMP (229 mL), and DMAP (979 mg) and DIPCI (4.97 mL) were added to the solution at 25° C. The mixture was stirred for two nights. The reaction liquid was added dropwise to diisopropyl ether (6.0 L), and the mixture was stirred. A precipitate was collected by filtration and dried in a vacuum, and a solid (28.8 g) thus obtained was dissolved in DMF (404 mL). An ion exchange resin (95.1 mL) was added to the solution, the mixture was stirred for one hour, and then the ion exchange resin was separated by filtration. The filtrate was added dropwise to diisopropyl ether (13.0 L), and the mixture was stirred. A precipitate was collected by filtration and dried in a vacuum, and a solid thus obtained was dissolved in acetonitrile (294 mL). Subsequently, purified water (294 mL) was added to the solution, and the mixture was concentrated under reduced pressure and then freeze-dried. Thus, Compound 12 (27.3 g) was obtained. The tacrolimus content of Compound 12 was calculated to be 3.24%.

Example 5

Polymeric derivative in which in regard to General Formula (2), $R_1$ represents a n-butyl group; $R_2$ represents an acetyl group; $R_3$ represents a residue of an alcoholic hydroxy group of tacrolimus; $R_4$ represents a structure of General Formula (5); $R_5$ represents an isopropylaminocarbonylisopropylamino group; $R_{11}$ represents a methyl group; $R_{12}$ represents a trimethylene group; $X_1$ represents a bond; $X_2$ represents a —NH— group; the average values of o and p are each 272; the average value of f+g+h+i+j+k+l+m+n is 78; the average value of f+g is 7.4; and the average value of h+i is 10.1 (Compound 13)

Compound 4 (83.2 mg) and tacrolimus (150 mg) were dissolved in NMP (7.5 mL), and DMAP (44.1 mg) and DIPCI (223 μL) were added to the solution at 25° C. The mixture was stirred for one hour, and then a polyethylene glycol having a methoxy group at one end and a 3-aminopropyl group at another end (SUNBRIGHT MEPA-12T, manufactured by NOF Corp., average molecular weight 12 kilodaltons, 1.12 g) was added to the mixture. The mixture was heated to 35° C. and was stirred overnight. The reaction liquid was added dropwise to diisopropyl ether (225 mL), and the mixture was stirred overnight. A precipitate was collected by filtration and dried in a vacuum, and a solid thus obtained was dissolved in acetonitrile (40 mL). Purified water (40 mL) was added to the solution, and an ion exchange resin (20 mL) was added thereto. The mixture was stirred under ice cooling, and then the ion exchange resin was separated by filtration. The filtrate was concentrated under reduced pressure and then freeze-dried, and thus Compound 13 (1.16 g) was obtained. The tacrolimus content of Compound 13 was calculated to be 4.40%.

Example 6

Polymeric derivative in which in regard to General Formula (2), $R_1$ represents a n-butyl group; $R_2$ represents an acetyl group; $R_3$ represents a residue of an alcoholic hydroxy group of tacrolimus; $R_4$ represents a structure of General Formula (5); $R_5$ represents an isopropylaminocarbonylisopropylamino group; $R_{11}$ represents a methyl group; $R_{12}$ represents a trimethylene group; $X_1$ represents a bond; $X_2$ represents a —NH— group; the average values of o and p are each 272; the average value of f+g+h+i+j+k+l+m+n is 112; the average value of f+g is 10.4; and the average value of h+i is 14.6 (Compound 14)

Compound 5 (85.8 mg) and tacrolimus (150 mg) were dissolved in NMP (7.5 mL), and DMAP (45.6 mg) and DIPCI (230 μL) were added to the solution at 25° C. The mixture was stirred for one hour, and then a polyethylene glycol having a methoxy group at one end and a 3-aminopropyl group at another end (SUNBRIGHT MEPA-12T, manufactured by NOF Corp., average molecular weight 12 kilodaltons, 1.12 g) was added thereto. The mixture was heated to 35° C. and was stirred overnight. The reaction liquid was added dropwise to diisopropyl ether (225 mL), and the mixture was stirred overnight. A precipitate was collected by filtration and dried in a vacuum, and a solid thus obtained was dissolved in acetonitrile (40 mL). Purified water (40 mL) was added to the solution, and an ion exchange resin (20 mL) was added thereto. The mixture was stirred under ice cooling, and then the ion exchange resin was separated by filtration. The filtrate was concentrated under reduced pressure and then freeze-dried. Thus, Compound 14 (1.18 g) was obtained. The tacrolimus content of Compound 14 was calculated to be 4.41%.

Example 7

Polymeric derivative in which in regard to General Formula (1), $R_1$ represents a structure of General Formula (6); $R_2$ represents an acetyl group; $R_3$ represents a residue of an alcoholic hydroxy group of tacrolimus; $R_4$ represents a structure of General Formula (5); $R_5$ represents an isopropylaminocarbonylisopropylamino group; $R_{11}$ and $R_{13}$ each represent a methyl group; $R_{12}$ and $R_{14}$ each represent a trimethylene group; $X_1$ represents a bond; $X_2$ represents a —NH— group; the average values of o and p are each 272; the average value of a+b+c+d+e is 40.2; the average value of a is 5.9; and the average value of b is 5.0 (Compound 15)

Compound 7 (3.30 g), tacrolimus (4.81 g), and a polyethylene glycol having methoxy group at one end and a 3-aminopropyl group at another end (SUNBRIGHT MEPA-12T, manufactured by NOF Corp., average molecular weight 12 kilodaltons, 11.9 g) were dissolved in NMP (160 mL), and DMAP (500 mg) and DIPCI (2.47 mL) were added to the solution at 35° C. The mixture was stirred for two nights. The reaction liquid was added dropwise to diisopropyl ether (4.8 L), and the mixture was stirred. A precipitate was collected by filtration and dried in a vacuum, and thus a solid (15.1 g) was obtained. The solid (15.0 g) thus obtained was dissolved in DMF (210 mL), and an ion exchange resin (50 mL) was added to the solution. The mixture was stirred for one hour, and then the ion exchange resin was separated by filtration. The filtrate was added dropwise to diisopropyl ether (6.8 L), and the mixture was stirred. A precipitate was collected by filtration and dried in a vacuum, and thus a solid (14.2 g) was obtained. The solid (13.7 g) thus obtained was dissolved in acetonitrile (275 mL), and then purified water (275 mL) was added to the solution. The mixture was concentrated under reduced pressure and then freeze-dried, and thus Compound 15 (12.4 g) was obtained. The tacrolimus content of Compound 16 was calculated to be 5.74%.

Example 8

Polymeric derivative in which in regard to General Formula (1), $R_1$ represents a structure of General Formula (6); $R_2$ represents an acetyl group; $R_3$ represents a residue of an alcoholic hydroxy group of tacrolimus; $R_4$ represents a structure of General Formula (5); $R_5$ represents an isopropylaminocarbonylisopropylamino group; $R_{11}$ and $R_{13}$ each represent a methyl group; $R_{12}$ and $R_{14}$ each represent a trimethylene group; $X_1$ represents a bond; $X_2$ represents a —NH— group; the average values of o and p are each 272; the average value of a+b+c+d+e is 87; the average value of a is 19.4; and the average value of b is 5.0 (Compound 16)

Compound 6 (157 mg), tacrolimus (375 mg), and a polyethylene glycol having a methoxy group at one end and a 3-aminopropyl group at another end (SUNBRIGHT MEPA-12T, manufactured by NOF Corp., average molecular weight 12 kilodaltons, 425 mg) were dissolved in NMP (5.5 mL), and DMAP (38.0 mg) and DIPCI (191 µL) were added to the solution at 35° C. The mixture was stirred for two nights. The reaction liquid was added dropwise to diisopropyl ether (165 mL), and the mixture was stirred. A precipitate was collected by filtration and dried in a vacuum, and a solid thus obtained was dissolved in acetonitrile (13 mL). Purified water (13 mL) was added to the solution, and an ion exchange resin (6.5 mL) was added thereto. The mixture was stirred under ice cooling, and then the ion exchange resin was separated by filtration. The filtrate was concentrated under reduced pressure and then freeze-dried, and thus Compound 16 (630 mg) was obtained. The tacrolimus content of Compound 16 was calculated to be 14.9%.

Example 9

Polymeric derivative in which in regard to General Formula (1), $R_1$ represents a structure of General Formula (6); $R_2$ represents an acetyl group; $R_3$ represents a residue of an alcoholic hydroxy group of tacrolimus; $R_4$ represents a structure of General Formula (5); $R_5$ represents an isopropylaminocarbonylisopropylamino group; $R_{11}$ and $R_{13}$ each represent a methyl group; $R_{12}$ and $R_{14}$ each represent a trimethylene group; $R_{13}$ represents a methyl group; $R_{14}$ represents a trimethylene group; $X_1$ represents a bond; $X_2$ represents a —NH— group; the average values of o and p are each 272; the average value of a+b+c+d+e is 90.0; the average value of a is 21.6; and the average value of b is 5.3 (Compound 17)

Compound 8 (3.0 g), tacrolimus (7.27 g), and a polyethylene glycol having a methoxy group at one end and a 3-aminopropyl group at another end (SUNBRIGHT MEPA-12T, manufactured by NOF Corp., average molecular weight 12 kilodaltons, 8.50 g) were dissolved in NMP (80.3 mL), and DMAP (733 mg) and DIPCI (3.72 mL) were added to the solution at 35° C. The mixture was stirred for two nights. The reaction liquid was added dropwise to diisopropyl ether (3,150 mL), and the mixture was stirred. A precipitate was collected by filtration and dried in a vacuum, and a solid (14.0 g) thus obtained was dissolved in DMF (196 mL). An ion exchange resin (46 mL) was added to the solution, the mixture was stirred, and then the ion exchange resin was separated by filtration. The filtrate was added dropwise to diisopropyl ether (6.3 L), and the mixture was stirred. A precipitate was collected by filtration and dried in a vacuum, and thus Compound 17 (12.9 g) was obtained. The tacrolimus content of Compound 17 was calculated to be 16.6%.

Comparative Example 1

Tacrolimus-Bonded Polyethylene Glycol-αβ-Polyaspartic Acid Block Copolymer (Compound 18)

Compound 2 (350 mg) and tacrolimus (366 mg) were dissolved in DMF (6.0 mL), and DMAP (10.9 mg) and DIPCI (315 µL) were added to the solution at 15° C. The mixture was stirred overnight. The reaction liquid was added dropwise to diisopropyl ether (180 mL), and the mixture was stirred. A precipitate was collected by filtration and dried in a vacuum, and a solid thus obtained was dissolved in acetonitrile (17 mL). Subsequently, purified water (17 mL) and an ion exchange resin (7 mL) were added to the solution, and the mixture was stirred for 3 hours under ice cooling. Subsequently, the ion exchange resin was separated by filtration. The filtrate was concentrated under reduced pressure and then freeze-dried. Thus, Compound 18 (499 mg) represented by the following Formula (12) was obtained. The tacrolimus content of Compound 18 was calculated to be 33.2%.

$$CH_3-O-(CH_2CH_2O)_t-(CH_2)_3-[(NHCOCH)_q-(NHCOCH_2CH)_r \underset{CH_2CO-R_{15}}{\overset{CO-R_{15}}{|}}]$$

$$-(NHCOCH)_s-(NHCOCH_2CH)_u-(NHCOCH)_v-(NHCOCH_2CH)_w-(NCOCH)_x]-NH-Ac$$
with side groups $CH_2CO-R_{16}$, $CO-R_{16}$, $CH_2CO_2H$, $CO_2H$, and $OC-CH_2$ / $OC-CH_2$ (12)

In the formula, the average value of t is 272; the average value of q+r+s+u+v+w+x is 42.8; the average value of q+r I 10.0; $R_{15}$ represents a residue of an alcoholic hydroxy group of tacrolimus; and $R_{16}$ represents an isopropylaminocarbonylisopropylamino group.

The tacrolimus content of the compound according to the present invention was calculated from the consumption rate of tacrolimus in the reaction solution measured under the following HPLC conditions.

Analysis conditions for HPLC

Column: Shim-pack XR-ODSIII, 2.04×200 mm

Column temperature: 40° C.

Eluent Liquid A: 0.1% aqueous solution of phosphoric acid, Liquid B: acetonitrile Liquid A/Liquid B=80/20

Flow rate: 0.5 mL/min

Detector (detection wavelength): UV (254 nm)

Alternatively, the tacrolimus content was calculated by subjecting the polymeric derivative of tacrolimus to acid hydrolysis, derivatizing pipecolic acid, which is a decomposition product of free tacrolimus, and quantitatively analyzing the derivative under the following HPLC conditions.

Analysis conditions for HPLC

Column: Shim-pack XR-ODSIII, 2.04×200 mm

Column temperature: 40° C.

Eluent Liquid A: 0.1% aqueous solution of phosphoric acid, Liquid B: acetonitrile Gradient elution at Liquid A/Liquid B=from 80/20 to 10/90

Flow rate: 0.5 mL/min

Detector (detection wavelength): Fluorescence (excitation wavelength: 450 nm, fluorescence wavelength: 590 nm)

Test Example 1

Test on Drug Releasability into Phosphate Buffered Physiological Saline

The compounds of Examples 1 to 9 and Comparative Example 1 were respectively dissolved in phosphate buffered physiological saline (pH 7.4) to a concentration of 1.0 mg/mL, and the solutions were left to stand at a constant temperature of 37° C. The amount of released tacrolimus was measured over time by HPLC, and the proportion of the amount of released tacrolimus with respect to the total amount of tacrolimus in the compound used was determined. The results for Example 1 and Comparative Example 1 are presented in FIG. 1, the results for Examples 1, 2, 5, 6, and 8 are presented in FIG. 2, and the results for Examples 3, 4, 7, and 9 are presented in FIG. 3.

As a result, it was found that the compounds of Examples 1 to 6 exhibited rapid release of the drug in the absence of enzymes, compared to the compound of Comparative Example 1. Furthermore, it was found that the compounds of Examples 7 to 9 exhibited slow release of the drug in the absence of enzyme, compared to the compounds of Examples 1 to 6.

Test Example 2

Blood Concentration Profile in Rats (1)

Eight-week old female SD rats (Charles River Laboratories Japan, Inc.) were grouped such that each group included two animals, and the rats were intravenously administered with tacrolimus or one of the compounds of Examples 1, 2 and 8 and Comparative Example 1 once at a dose of 5 mg/kg through the caudal vein. At 5 minutes, 1 hour, 6 hours, 24 hours, and 72 hours after administration, blood was collected through the jugular vein under isoflurane anesthesia successively in an amount of 0.3 mL each time, and the tacrolimus concentration in the collected blood was measured. The results for Examples 1, 2 and 8, Comparative Example 1, and tacrolimus are presented in FIG. 4. Furthermore, the blood concentration parameters for the various compounds are presented in Table 2. However, the results for Examples 1, 2 and 8 and Comparative Example 1 are the concentrations and parameters for tacrolimus cut out from micelles.

TABLE 2

| Group | Dose (mg/kg) | T½ (hr) | Tmax (hr) | Cmax (ng/mL) | C72 h (ng/mL) | AUCinf. (hr · ng/mL) | MRTinf. (hr) |
|---|---|---|---|---|---|---|---|
| Example 1 | 5 | 14.6 | 0.0833 | 231 | 3.34 | 2430 | 19.0 |
| Example 2 | 5 | 16.1 | 0.0833 | 407 | 5.27 | 3040 | 20.8 |
| Example 8 | 5 | 16.0 | 0.0833 | 133 | 1.96 | 1060 | 20.7 |
| Comparative Example 1 | 5 | 9.57 | 0.0833 | 280 | 0.361 | 1050 | 11.6 |
| Tacrolimus | 5 | 7.51 | 0.0833 | 2430 | 0.273 | 5400 | 4.12 |

From these results, Examples 1, 2 and 8 and Comparative Example 1 show prolongation of the blood concentration half-life and the MRTinf., compared to tacrolimus, and it is obvious that retentivity in blood was enhanced by converting tacrolimus into a polymer derivative.

Furthermore, Examples 1, 2 and 8 exhibited longer blood concentration half-lives and larger MRTinf. values, compared to Comparative Example 1.

Test Example 3

Blood Concentration Profile in Rats (2)

Eight-week old female SD rats (Charles River Laboratories Japan, Inc.) were grouped such that each group included two animals, and the rats were intravenously administered with one of the compounds of Examples 3, 7, and 9 once at a dose of 15 mg/kg through the caudal vein. At 5 minutes, 1 hour, 6 hours, 24 hours, and 72 hours after administration, blood was collected through the jugular vein under isoflurane anesthesia successively in an amount of 0.2 mL each time, and the tacrolimus concentration in the collected blood was measured. The results for Examples 3, 7, and 9 are presented in FIG. 5. Furthermore, the blood concentration parameters for the various compounds are presented in Table 3. However, the results for Examples 3, 7, and 9 are the concentrations and parameters for tacrolimus cut out from micelles.

TABLE 3

| Group | Dose (mg/kg) | T½ (hr) | Tmax (hr) | Cmax (ng/mL) | C72 h (ng/mL) | AUCinf. (hr · ng/mL) | MRTinf. (hr) |
| --- | --- | --- | --- | --- | --- | --- | --- |
| Example 3 | 15 | 16.5 | 0.0833 | 1340 | 23.5 | 12500 | 20.3 |
| Example 7 | 15 | 15.4 | 0.0833 | 1100 | 4.29 | 3490 | 12.8 |
| Example 9 | 15 | 19.5 | 0.0833 | 211 | 6.00 | 2410 | 25.7 |

From these results, Examples 3, 7, and 9 all exhibited longer blood concentration half-lives and large MRTinf. values.

Test Example 4

Anti-Inflammatory Effect for Rat Collagen-Induced Arthritis (1)

0.3 mg of bovine articular cartilage-derived type II collagen (immunological grade; Collagen Research Center, Ltd.) was intradermally administered on the dorsal side of nine-week old female DA rats (Japan SLC, Inc.), and thereby collagen-induced arthritis was induced in the rats. On the day of type II collagen sensitization and on the 7$^{th}$ day, 14$^{th}$ day, and 21$^{st}$ day after sensitization, physiological saline solutions of the compounds of Comparative Example 1, Examples 1, 2 and 8 (5 mg/kg) were each intravenously administered to five animals in each group through the caudal vein. As a control, a non-administered group was provided. Determination of arthritis was made by scoring based on visual inspection. The results for the compound of Comparative Example 1 are presented in FIG. 6, the results for the compound of Example 1 are presented in FIG. 7, and the results for the compounds of Examples 2 and 8 are presented in FIG. 8. The average arthritis scores on the 28$^{th}$ day or 29$^{th}$ day after collagen sensitization are presented in Table 4.

From the time point after the sensitization with bovine articular cartilage-derived type II collagen, the progress of inflammation in the right hind limb and the left hind limb was monitored. It was determined that the onset of collagen-induced arthritis occurred when reddening was recognized in the toes of the right hind limb or the left hind limb. The extent of arthritis was evaluated in six stages according to the following scores from 0 to 5. 0: No change; 1: reddening at one or more sites in the right hind limb or the left hind limb; 2: reddening and slight edema at one or more sites in the right hind limb or the left hind limb; 3: edema in the entirety of the right hind limb or the left hind limb; 4: severe edema in the entirety of the right hind limb or the left hind limb; 5: mobility of the tarsal joint in the right hind limb or the left hind limb is restricted compared to the normal condition (deformation of the joint). Between the right hind limb and the left hind limb, the value of the limb with a higher arthritis score was adopted as the arthritis score for the individual.

Test Example 5

Anti-Inflammatory Effect for Rat Collagen-Induced Arthritis (2)

Collagen-induced arthritis was induced in DA rats by a method similar to that of Test Example 4. On the day of type II collagen sensitization and on the 14$^{th}$ day after sensitization, physiological saline solutions of the compounds of Examples 3, 7, and 9 (15 mg/kg) were each intravenously administered to five animals in each group through the caudal vein. As a control, a non-administered group was provided. Determination of arthritis was made by scoring based on visual inspection. The results are presented in FIG. 9. The average arthritis scores on the 28$^{th}$ day after collagen sensitization are presented in Table 4.

TABLE 4

| Group | 5 mg/kg, q7 d × 4 Arthritis score (28 d) | 15 mg/kg, q14 d × 2 Arthritis score (28 d) |
| --- | --- | --- |
| Comparative Example 1 | 2.6* | nt |
| Example 1 | 0.0 | nt |
| Example 2 | 0.0 | nt |
| Example 3 | nt | 0.0 |
| Example 7 | nt | 1.8 |
| Example 8 | 0.8 | nt |
| Example 9 | nt | 0.6 |

*Score 29 d
nt; no test

From the results of Test Examples 4 and 5, the onset of arthritis was recognized in the non-administered group. Meanwhile, the compounds of the present invention suppressed the onset of arthritis, compared to the non-administered group. Furthermore, in Examples 1, 2, and 8, a strong suppressive effect against arthritis was recognized, compared to Comparative Example 1, by introducing polyethylene glycol in the side chains.

The invention claimed is:

1. A polymeric derivative of tacrolimus, comprising a polyaspartic acid derivative, a polyethylene glycol segment, and tacrolimus, wherein the polyethylene glycol segment and an alcoholic hydroxy group of tacrolimus are bonded to side-chain carboxy groups of the polyaspartic acid derivative.

2. The polymeric derivative of tacrolimus according to claim 1, wherein the polymeric derivative is represented by the following General Formula (1):

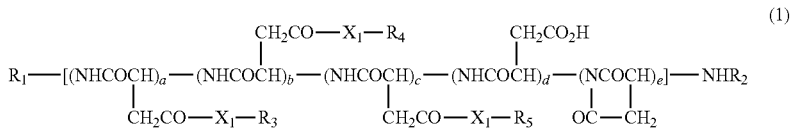

wherein $R_1$ represents a group selected from a group consisting of a hydrogen atom, a (C1-C8) alkyl group, and a polyethylene glycol segment; $R_2$ represents a group selected from a group consisting of a hydrogen atom, a (C1-C8) acyl group, and a (C1-C8) alkoxycarbonyl group; $R_3$ represents a residue of an alcoholic hydroxy group of tacrolimus; $R_4$ represents a polyethylene glycol segment; $R_5$ represents —N($R_6$)CONH ($R_7$) (wherein $R_6$ and $R_7$, which may be identical or different, each represent a (C3-C6) cyclic alkyl group or a (C1-C5) alkyl group which may be substituted with a tertiary amino group); $X_1$ represents a bond or a linking group; a and b each represent an integer from 1 to 299; c, d, and e each represent zero or an integer of 298 or less; a+b+c+d+e represents an integer from 2 to 300; and the order of arrangement of the various repeating units of the polyaspartic acid derivative is arbitrary.

3. The polymeric derivative of tacrolimus according to claim 1, wherein the polymeric derivative is represented by the following General Formula (2):

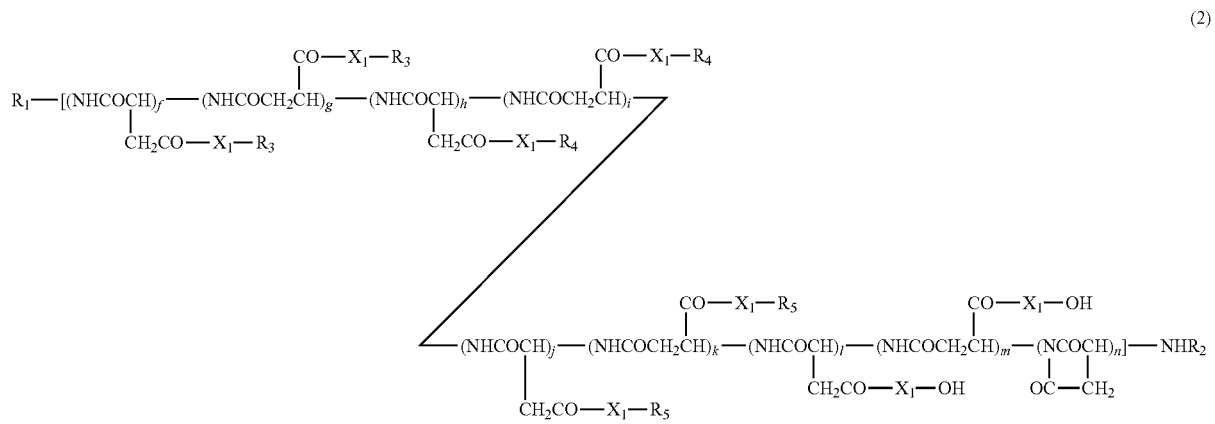

wherein $R_1$ represents a group selected from a group consisting of a hydrogen atom, a (C1-C8) alkyl group, and a polyethylene glycol segment; $R_2$ represents a group selected from a group consisting of a hydrogen atom, a (C1-C8) acyl group, and a (C1-C8) alkoxycarbonyl group; $R_3$ represents a residue of an alcoholic hydroxy group of tacrolimus; $R_4$ represents a polyethylene glycol segment; $R_5$ represents —N($R_6$)CONH ($R_7$) (wherein $R_6$ and $R_7$, which may be identical or different, each represent a (C3-C6) cyclic alkyl group or a (C1-C5) alkyl group which may be substituted with a tertiary amino group); $X_1$ represents a bond or a linking group; f, g, h, and i each represent zero or an integer of 299 or less; f+g and h+i each represent an integer from 1 to 299 or less; j, k, l, m, and n each represent zero or an integer of 298 or less; f+g+h+i+j+k+l+m+n represents an integer from 2 to 300; and the order of arrangement of the various repeating units of the polyaspartic acid derivative is arbitrary.

4. The polymeric derivative of tacrolimus according to claim 2, wherein $X_1$ represents a bond.

5. The polymeric derivative of tacrolimus according to claim 2, wherein $X_1$ represents an aspartic acid derivative.

6. The polymeric derivative of tacrolimus according to claim 2, wherein $X_1$ is represented by the following General Formula (3) or General Formula (4):

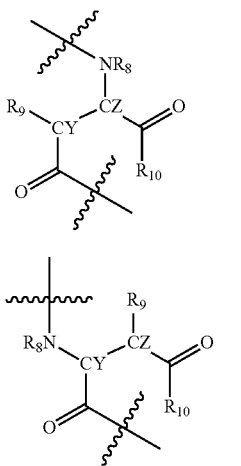

wherein $R_8$ and $R_9$ each independently represent a hydrogen atom or a (C1-C8) alkyl group; $R_{10}$ represents one or more groups selected from a group consisting of an amino group, a linear, branched or cyclic (C1-C20) alkylamino group which may have a substituent, a linear, branched or cyclic (C7-C20) aralkylamino group which may have a substituent, a (C5-C20) aromatic amino group which may have a substituent, and an amino acid residue having a protected carboxy group; and CY—CZ represents CH—CH or C=C (double bond).

7. The polymeric derivative of tacrolimus according to claim 6, wherein $R_8$ and $R_9$ both represent a hydrogen atom; and CY—CZ represents CH—CH.

8. The polymeric derivative of tacrolimus according to claim 2, wherein the polyethylene glycol segment of $R_4$ is represented by the following General Formula (5):

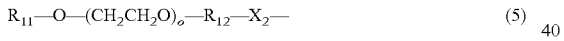

wherein $R_{11}$ represents a hydrogen atom, or a linear, branched or cyclic (C1-C6) alkyl group which may have a substituent; $R_{12}$ represents a (C2-C6) alkylene group; $X_2$ represents a functional group bondable to a side-chain carboxy group of the polyaspartic acid derivative; and o represents an integer from 5 to 11,500.

9. The polymeric derivative of tacrolimus according to claim 2, wherein $R_1$ represents a (C1-C6) alkyl group or a polyethylene glycol segment represented by the following General Formula (6):

wherein $R_{13}$ represents a hydrogen atom, or a linear, branched or cyclic (C1-C6) alkyl group which may have a substituent; $R_{14}$ represents a (C2-C6) alkylene group; and p represents an integer from 5 to 11,500.

10. The polymeric derivative of tacrolimus according to claim 2, wherein $R_2$ represents a (C1-C6) acyl group; o represents an integer from 10 to 3,000; and (a+b+c+d+e) or (f+g+h+i+j+k+l+m+n) represents an integer from 4 to 250.

11. The polymeric derivative of tacrolimus according to claim 10, wherein $R_2$ represents a (C1-C3) acyl group; o represents an integer from 20 to 1,500; and (a+b+c+d+e) or (f+g+h+i+j+k+l+m+n) represents an integer from 8 to 200.

12. The polymeric derivative of tacrolimus according to claim 2, wherein $R_1$ represents a methyl group, and $R_2$ represents an acetyl group.

13. A method for producing the polymeric derivative of tacrolimus according to claim 2, wherein an alcoholic hydroxy group of tacrolimus and a polyethylene glycol segment are bonded to side-chain carboxy groups of a polyaspartic acid derivative via an ester bond, an amide bond, and/or a thioester bond using a dehydration condensing agent in an organic solvent.

14. A macrolide immunosuppressant comprising the polymeric derivative of tacrolimus according to claim 2 as an active ingredient.

15. The polymeric derivative of tacrolimus according to claim 3, wherein $X_1$ represents a bond.

16. The polymeric derivative of tacrolimus according to claim 3, wherein $X_1$ represents an aspartic acid derivative.

17. The polymeric derivative of tacrolimus according to claim 3, wherein $X_1$ is represented by the following General Formula (3) or General Formula (4):

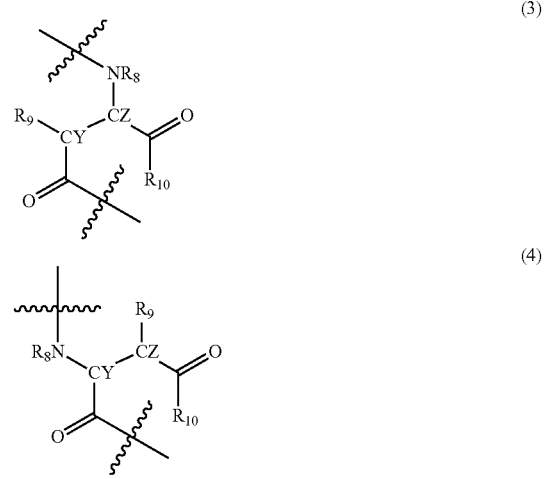

wherein $R_8$ and $R_9$ each independently represent a hydrogen atom or a (C1-C8) alkyl group; $R_{10}$ represents one or more groups selected from a group consisting of an amino group, a linear, branched or cyclic (C1-C20) alkylamino group which may have a substituent, a linear, branched or cyclic (C7-C20) aralkylamino group which may have a substituent, a (C5-C20) aromatic amino group which may have a substituent, and an amino acid residue having a protected carboxy group; and CY—CZ represents CH—CH or C=C (double bond).

18. The polymeric derivative of tacrolimus according to claim 17, wherein $R_8$ and $R_9$ both represent a hydrogen atom; and CY—CZ represents CH—CH.

19. The polymeric derivative of tacrolimus according to claim 3, wherein the polyethylene glycol segment of $R_4$ is represented by the following General Formula (5):

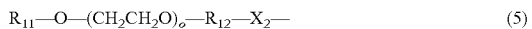

wherein $R_{11}$ represents a hydrogen atom, or a linear, branched or cyclic (C1-C6) alkyl group which may have a substituent; $R_{12}$ represents a (C2-C6) alkylene group; $X_2$ represents a functional group bondable to a side-chain carboxy group of the polyaspartic acid derivative; and o represents an integer from 5 to 11,500.

20. The polymeric derivative of tacrolimus according to claim 3, wherein $R_1$ represents a (C1-C6) alkyl group or a polyethylene glycol segment represented by the following General Formula (6):

$$R_{13}-O-(CH_2CH_2O)_p-R_{14}- \quad (6)$$

wherein $R_{13}$ represents a hydrogen atom, or a linear, branched or cyclic (C1-C6) alkyl group which may have a substituent; $R_{14}$ represents a (C2-C6) alkylene group; and p represents an integer from 5 to 11,500.

21. The polymeric derivative of tacrolimus according to claim 3, wherein $R_2$ represents a (C1-C6) acyl group; o represents an integer from 10 to 3,000; and (a+b+c+d+e) or (f+g+h+i+j+k+l+m+n) represents an integer from 4 to 250.

22. The polymeric derivative of tacrolimus according to claim 21, wherein $R_2$ represents a (C1-C3) acyl group; o represents an integer from 20 to 1,500; and (a+b+c+d+e) or (f+g+h+i+j+k+l+m+n) represents an integer from 8 to 200.

23. The polymeric derivative of tacrolimus according to claim 3, wherein $R_1$ represents a methyl group, and $R_2$ represents an acetyl group.

24. A method for producing the polymeric derivative of tacrolimus according to claim 3, wherein an alcoholic hydroxy group of tacrolimus and a polyethylene glycol segment are bonded to side-chain carboxy groups of a polyaspartic acid derivative via an ester bond, an amide bond, and/or a thioester bond using a dehydration condensing agent in an organic solvent.

25. A macrolide immunosuppressant comprising the polymeric derivative of tacrolimus according to claim 3 as an active ingredient.

* * * * *